(12) United States Patent
Gaeta

(10) Patent No.: US 10,774,368 B2
(45) Date of Patent: *Sep. 15, 2020

(54) NUCLEIC ACID PRESERVATION SOLUTION AND METHODS OF MANUFACTURE AND USE

(71) Applicant: SPECTRUM SOLUTIONS L.L.C., Draper, UT (US)

(72) Inventor: Federico Carlos Arejola Gaeta, Torre Molinos (ES)

(73) Assignee: Spectrum Solutions L.L.C., Draper, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/176,210

(22) Filed: Oct. 31, 2018

(65) Prior Publication Data

US 2019/0062806 A1 Feb. 28, 2019

Related U.S. Application Data

(63) Continuation of application No. 15/872,791, filed on Jan. 16, 2018, now Pat. No. 10,174,362.

(60) Provisional application No. 62/446,818, filed on Jan. 16, 2017.

(51) Int. Cl.
*C12Q 1/6806* (2018.01)
*C12N 15/10* (2006.01)

(52) U.S. Cl.
CPC ....... *C12Q 1/6806* (2013.01); *C12N 15/1003* (2013.01)

(58) Field of Classification Search
CPC .......................... C12Q 1/6806; C12N 15/1003
See application file for complete search history.

(56) References Cited

U.S. PATENT DOCUMENTS

| | | | | |
|---|---|---|---|---|
| 4,308,264 | A | * | 12/1981 | Conway ............... A61K 9/0019 514/167 |
| 4,808,328 | A | * | 2/1989 | Flohr ..................... C11D 3/485 424/667 |
| 4,925,796 | A | * | 5/1990 | Bergh .................. C07K 1/1077 435/193 |
| 5,110,493 | A | * | 5/1992 | Cherng-Chyi ....... A61K 9/0048 514/413 |
| 5,346,999 | A | * | 9/1994 | Cathcart .............. B01J 19/0046 436/175 |
| 5,648,215 | A | * | 7/1997 | West ...................... A61K 31/70 435/15 |
| 5,747,339 | A | * | 5/1998 | Okayama ............. C07K 14/005 435/350 |
| 5,945,515 | A | * | 8/1999 | Chomczynski .... C12N 15/1003 435/270 |
| 5,981,831 | A | * | 11/1999 | Chengappa .......... C12N 9/2468 536/23.6 |
| 6,528,641 | B2 | | 3/2003 | Lader |
| 7,029,840 | B2 | | 4/2006 | McMillian |
| 7,270,953 | B2 | | 9/2007 | Hollander et al. |
| 7,482,116 | B2 | | 1/2009 | Birnboim |
| 7,569,342 | B2 | | 8/2009 | Baker |
| 8,080,645 | B2 | | 12/2011 | Fischer et al. |
| 8,084,443 | B2 | | 12/2011 | Fischer et al. |
| 8,404,439 | B2 | | 3/2013 | Conrad |
| 8,415,330 | B2 | | 4/2013 | Fischer et al. |
| 8,470,536 | B2 | | 6/2013 | Birnboim et al. |
| 8,669,240 | B2 | | 3/2014 | Fischer et al. |
| 9,012,135 | B2 | | 4/2015 | Haj-Ahmad |
| 9,212,399 | B2 | | 12/2015 | Fischer et al. |
| 9,376,709 | B2 | | 6/2016 | Whitney et al. |
| 9,416,416 | B2 | | 8/2016 | Fischer et al. |
| 9,683,256 | B2 | * | 6/2017 | Fischer .............. C12N 15/1003 |
| 2004/0019196 | A1 | * | 1/2004 | Bair, Jr. .............. C12N 15/1003 536/25.4 |
| 2004/0043505 | A1 | * | 3/2004 | Walenciak ....... A61B 5/150389 436/174 |
| 2005/0042656 | A1 | * | 2/2005 | Davis .................. C12N 15/1006 435/6.13 |
| 2006/0014177 | A1 | * | 1/2006 | Hogan ............... C12N 15/1006 435/6.14 |
| 2006/0078894 | A1 | * | 4/2006 | Winkler ............... C12Q 1/6844 435/6.18 |
| 2006/0141488 | A1 | | 6/2006 | Huang et al. |
| 2007/0202497 | A1 | * | 8/2007 | Renuart ............... C12Q 1/6834 435/6.12 |
| 2008/0044883 | A1 | * | 2/2008 | Walker ................. C12N 9/1252 435/194 |
| 2008/0064108 | A1 | | 3/2008 | Baker |
| 2008/0124728 | A1 | | 5/2008 | Baker |
| 2009/0233309 | A1 | * | 9/2009 | Fischer ................... A61P 31/10 435/6.18 |
| 2009/0305422 | A1 | | 12/2009 | Baker |

(Continued)

FOREIGN PATENT DOCUMENTS

WO 2007/049326 A1 5/2007
WO WO-2008013885 A2 * 1/2008 ............. C12Q 1/686

(Continued)

OTHER PUBLICATIONS

M. Laulier et al., *An Easy Method for Preserving Nucleic Acids in Field Samples for Later Molecular and Genetic Studies without Refrigerating*, J. Evol. Bio., vol. 8, 1995, pp. 657-663.

(Continued)

*Primary Examiner* — Joseph G. Dauner
(74) *Attorney, Agent, or Firm* — Workman Nydegger

(57) ABSTRACT

Disclosed is nucleic acid preserving compositions and methods of manufacturing and using the same. Compositions include a carrier, a chaotropic agent, a buffering agent, a chelating agent, a surfactant, an alcohol, an acid, and a mucolytic agent. Compositions as aqueous solutions can include water as a carrier. Preferred embodiments include water, guanidine thiocyanate, Tris, EDTA, SLS, SDA 3C, HCl, and N-acetyl-L-cysteine. Some embodiments include a colored dye as a visual indicator. Methods of manufacturing include combining the components into a mixture, such as an aqueous solution. Methods of use include providing a biological sample that includes nucleic acid and contacting the biological sample with the composition. Kits include the composition disposed in a portion of a biological sample collection apparatus.

24 Claims, 1 Drawing Sheet

(56) References Cited

U.S. PATENT DOCUMENTS

| | | |
|---|---|---|
| 2010/0003748 A1 | 1/2010 | Baker |
| 2010/0120078 A1 | 5/2010 | Baker |
| 2010/0136542 A1 | 6/2010 | Lee et al. |
| 2010/0209927 A1* | 8/2010 | Menon ............... B01L 3/50273 435/6.16 |
| 2011/0014658 A1 | 1/2011 | Birnboim et al. |
| 2011/0236895 A1* | 9/2011 | Tanigami ............. C12Q 1/6806 435/6.11 |
| 2011/0256592 A1* | 10/2011 | Beckers ................ C12Q 1/686 435/91.5 |
| 2012/0115126 A1 | 5/2012 | Fisher et al. |
| 2013/0209997 A1 | 8/2013 | Whitney et al. |
| 2013/0260369 A1 | 10/2013 | Fischer et al. |
| 2014/0038174 A1 | 2/2014 | Fischer |
| 2014/0072976 A1 | 3/2014 | Baker |
| 2015/0252354 A1 | 9/2015 | Cepheid |
| 2015/0267245 A1 | 9/2015 | Hogan |
| 2016/0045918 A1* | 2/2016 | Lapham ........... G01N 35/00732 506/23 |
| 2016/0090619 A1* | 3/2016 | Murayama ............ B01L 3/502 422/527 |
| 2016/0108463 A1* | 4/2016 | Fischer ................ C12Q 1/6848 506/9 |
| 2016/0333339 A1* | 11/2016 | Fischer .................. C12Q 1/686 |
| 2016/0333394 A1 | 11/2016 | Conrad et al. |
| 2016/0338342 A1 | 11/2016 | Whitney et al. |
| 2016/0348153 A1 | 12/2016 | Narayanan et al. |
| 2017/0173537 A1* | 6/2017 | Gagnon ................... C07K 1/34 |

FOREIGN PATENT DOCUMENTS

| | | | |
|---|---|---|---|
| WO | WO-2009085355 A2 * | 7/2009 | ....... C12Q 2527/125 |
| WO | WO-2010123908 A1 * | 10/2010 | ...... C12Q 2523/113 |

OTHER PUBLICATIONS

International Search Report and Written Opinion dated May 15, 2018, issued in PCT Application No. PCT/US2018/13862, filed Jan. 16, 2018.

* cited by examiner

NUCLEIC ACID PRESERVATION SOLUTION AND METHODS OF MANUFACTURE AND USE

CROSS REFERENCE TO RELATED APPLICATIONS

This application is a Continuation of and claims priority to U.S. patent application Ser. No. 15/872,791, filed Jan. 16, 2018, entitled "Nucleic Acid Preservation Solution and Methods of Manufacture and Use," which claims the benefit of and priority to U.S. Prov. Pat. App. Ser. No. 62/446,818, filed Jan. 16, 2017, entitled "Nucleic Acid Preservation Solution and Methods of Manufacture and Use," the entirety of each of which is incorporated herein by reference.

BACKGROUND

1. Technical Field

The present disclosure relates to preserving nucleic acid. Specifically, the present disclosure relates to compositions and methods for preserving human nucleic acid in a biological sample for further analysis.

2. Related Technology

Nucleic acid can be extracted from biological samples that include cellular and/or cell-free nucleic acids. Extracted nucleic acid can be used for a variety of analytical purposes, including genealogical analysis. Extraction of nucleic acids from saliva can be particularly useful, as saliva sample collection is relatively non-invasive.

Nucleic acid-containing biological samples often need to be properly processed for specific types of nucleic acid analysis. Analytical techniques such as nucleic acid sequencing (e.g., next generation sequencing (NGS)), for example, may require specific processing or pre-processing steps that depend on the specific platform to be used. In some cases, the nucleic acid-containing biological samples may need to be processed in order to stabilize the sample or nucleic acid thereof. Stabilizing solutions are often added to nucleic acid-containing biological samples to ensure survival of a portion of the nucleic acids until analysis thereof can be performed.

Existing stabilizing solutions may not be optimal for certain types of analytical techniques or devices for performing the same. For instance, a stabilizing solution formulated for optimal or suitable analysis in a certain next generation sequencer, may not be optimal or suitable for analysis in other next generation sequencers. In some cases, improper formulation may produce or lead to analytical artifacts, high background signal (or noise), contamination and/or retention of microbial nucleic acids, and/or reduce the total potential yield of human nucleic acid.

Existing stabilizing solutions may also be deficient in controlling microbial life. Biological sample, such as saliva, often include and/or become contaminated with one or more microbes (e.g., bacteria, fungi, etc.). These microbes contain nucleic acids that may interfere or be detected along with the nucleic acid of the host or source of the biological sample. Preservation solutions may inadvertently stabilize microbial nucleic acids or even permit the growth of the microorganisms.

Accordingly, there continues to be a need for a universal nucleic acid stabilizing solution suitable for a variety of analytical techniques and devices and/or a solution that provides a better overall yield of nucleic acid and quality of sample, as compared to existing products.

BRIEF SUMMARY

Embodiments of the present disclosure solve one or more of the foregoing or other problems in the art with one or more embodiments comprising a nucleic acid preservation, stabilization, and/or preparation compositions, kits comprising the same, and methods of manufacturing and using the same. For instance, some embodiments of the present disclosure include compositions for preserving, stabilizing, and/or preparing nucleic acid in a biological sample. The composition can be suitable for use in a variety of analytical techniques and devices. The composition can yield high amounts of nucleic acid for subsequent analysis. For example, the composition can yield high amounts of human nucleic acid (e.g., DNA), preferably and/or optionally with low amounts of microbial (e.g., bacterial) nucleic acid (e.g., DNA) for subsequent analysis. The composition can comprise a solution or water-based (e.g., aqueous) liquid, optionally (light) blue in color, suitable for use in the stabilization of human nucleic acid (DNA) and prevention of bacterial contamination and for long term storage.

An embodiment of the present disclosure includes a nucleic acid preservation composition, comprising an aqueous carrier, a chaotropic agent, a buffering agent, a chelating agent, a surfactant, an alcohol, an acid; and a mucolytic agent. An embodiment can further include a visual indicator. In some embodiments, the aqueous carrier can be or comprise water, preferably filtered, purified, distilled, and/or deionized water. In some embodiments, the chaotropic agent can be or comprise guanidine and/or thiocyanate, preferably guanidine thiocyanate. In some embodiments, the buffering agent can be or comprise tris(hydroxymethyl)aminomethane (Tris), preferably Tris-HCl, more preferably Trizma® base. In some embodiments, the chelating agent can be or comprise ethyenediaminetetraacetic acid (EDTA), preferably as EDTA disodium salt, more preferably as EDTA disodium (salt) dihydrate. In some embodiments, the surfactant can be or comprise sodium lauroyl sarcosinate (SLS). In some embodiments, the alcohol can be or comprise a specially denatured alcohol (SDA) or a mixture of ethanol and isopropanol, preferably a mixture of about 95% ethanol, v/v and about 5% isopropanol, v/v, or SDA 3C. In some embodiments, the acid can be or comprise hydrochloric acid. In some embodiments, the mucolytic agent can be or comprise N-acetyl-L-cysteine. In some embodiments, the visual indicator can be or comprise a coloring agent, such as a dye (e.g., FD&C Blue No. 1).

An embodiment of the present disclosure includes a human nucleic acid preservation composition, comprising about 43.92% chaotropic agent (e.g., guanidine thiocyanate), w/w, about 2.65% buffering agent (e.g., Tris), w/w, about 0.81% chelating agent (e.g., EDTA disodium dihydrate), w/w, about 0.279% surfactant (e.g., SLS), w/w, about 17.73% alcohol (e.g., SDA 3C), w/w, about 0.093% mucolytic agent (e.g., N-acetyl-L-cysteine), w/w, about 0.4% acid (e.g., hydrochloric acid), w/w or acid qs to about pH 8.0; and/or about 34.12% carrier (e.g., an aqueous carrier comprising filtered, purified, distilled, and/or deionized water) or carrier qs to 100%. An embodiment can further include about 0.00037%, w/w, visual indicator (e.g., FD&C Blue No. 1) or equivalent thereof (e.g., 0.185%, w/w, of a 0.2%, w/w, visual indicator concentrate (e.g., in water)).

One or more embodiments can include 43.92% chaotropic agent (e.g., guanidine thiocyanate), w/w, ±10%, 2.65% buffering agent (e.g., Tris), w/w, ±10%, 0.81% chelating agent (e.g., EDTA or EDTA disodium (salt) dihydrate), w/w, ±10%, 0.279% surfactant (e.g., SLS), w/w, ±10%, 17.73% alcohol (e.g., SDA 3C or a mixture of 95% ethanol, v/v, ±10%, and 5% isopropanol, v/v, ±10%), w/w, ±10%, 0.093% mucolytic agent (e.g., N-acetyl-L-cysteine), w/w, ±10%, and/or acid (e.g., hydrochloric acid) qs to pH 8.0, ±10%, with a carrier (e.g., an aqueous carrier, preferably filtered, purified, distilled, and/or deionized water) qs to 100%. An embodiment can further include 0.00037%, w/w, ±10% visual indicator (e.g., FD&C Blue No. 1) or equivalent thereof (e.g., 0.185%, w/w, ±10%, of a 0.2%, w/w, ±10% visual indicator concentrate (e.g., in water)). In some embodiments, the amount of each component, ±10%, is further (limited to the recited amount) ±9%, preferably ±8%, more preferably ±7%, still more preferably ±6%, still more preferably ±5%, still more preferably ±4%, still more preferably ±3%, still more preferably ±2%, still more preferably ±1%.

One or more embodiments can include 20-50% chaotropic agent, w/w, 0.1-5% buffering agent, w/w, 0.05-2.5% chelating agent, w/w, 0.01-5% surfactant, w/w, 5-25% alcohol, w/w, 0.005-0.25% mucolytic agent, w/w, 0.005-5% acid or acid qs to pH 6.5-9.5, and/or 10-60% carrier or carrier qs to 100%. An embodiment can include 0.00005-0.5%, w/w, visual indicator (or 0.01-2.5%, w/w, of a 0.05-5%, w/w, visual indicator concentrate (e.g., in water)).

One or more embodiments can be (substantially) devoid of (additional or any) antimicrobial(s) (e.g., bactericidal and/or bacteriostatic) agent(s) (e.g., besides or other than the alcohol(s), chaotropic agent(s), surfactant(s)/detergent(s), and/or mucolytic agent(s)). One or more embodiments can be (substantially) devoid of (additional or any) ribonuclease inhibitor(s), or inhibitor(s) of ribonuclease (e.g., besides or other than the chaotropic agent(s)). One or more embodiments can be (substantially) devoid of (any) a protease(s).

Some embodiments include a method of stabilizing nucleic acid. The method can include providing a biological sample containing the nucleic acid and combining a composition of the present disclosure with the biological sample. The method can also include other processing steps known in the art. An embodiment of the present disclosure includes a method of stabilizing nucleic acid (e.g., human nucleic acid, such as human DNA). An embodiment comprises contacting a biological sample containing the nucleic acid with a composition of the present disclosure. In an embodiment, the biological sample comprises human saliva.

Some embodiments include a biological sample preservation kit. The kit can comprise a sample collection apparatus and a nucleic acid preservation composition. The sample collection apparatus can comprise a solution compartment. The nucleic acid preservation composition can be disposed in the solution compartment. An embodiment of the present disclosure includes a kit comprising a composition of the present disclosure disposed in a portion of a sample collection apparatus.

Some embodiments include a method of manufacturing a composition of the present disclosure. The method can include combining components of the present disclosure. The method can also include other manufacturing steps known in the art. An embodiment of the present disclosure includes a method of manufacturing a nucleic acid stabilization composition. An embodiment comprises obtaining a carrier and adding to the carrier components or ingredients of a composition of the present disclosure.

Additional features and advantages of exemplary embodiments of the present disclosure will be set forth in the description which follows, and in part will be obvious from the description, or may be learned by the practice of such exemplary embodiments. The features and advantages of such embodiments may be realized and obtained by means of the instruments and combinations particularly pointed out in the appended claims. These and other features will become more fully apparent from the following description and appended claims, or may be learned by the practice of such exemplary embodiments as set forth hereinafter.

BRIEF DESCRIPTION OF THE DRAWINGS

In order to describe the manner in which the above-recited and other advantages and features of the present disclosure can be obtained, a more particular description of the implementations briefly described above will be rendered by reference to specific implementations thereof, which are illustrated in the appended drawings. For better understanding, the like elements have been designated by like reference numbers throughout the figure(s). Understanding that these drawings depict only typical implementations of the invention and are not therefore to be considered to be limiting of its scope, the invention will be described and explained with additional specificity and detail through the use of the accompanying drawing(s) in which.

DETAILED DESCRIPTION

Figure 1A:
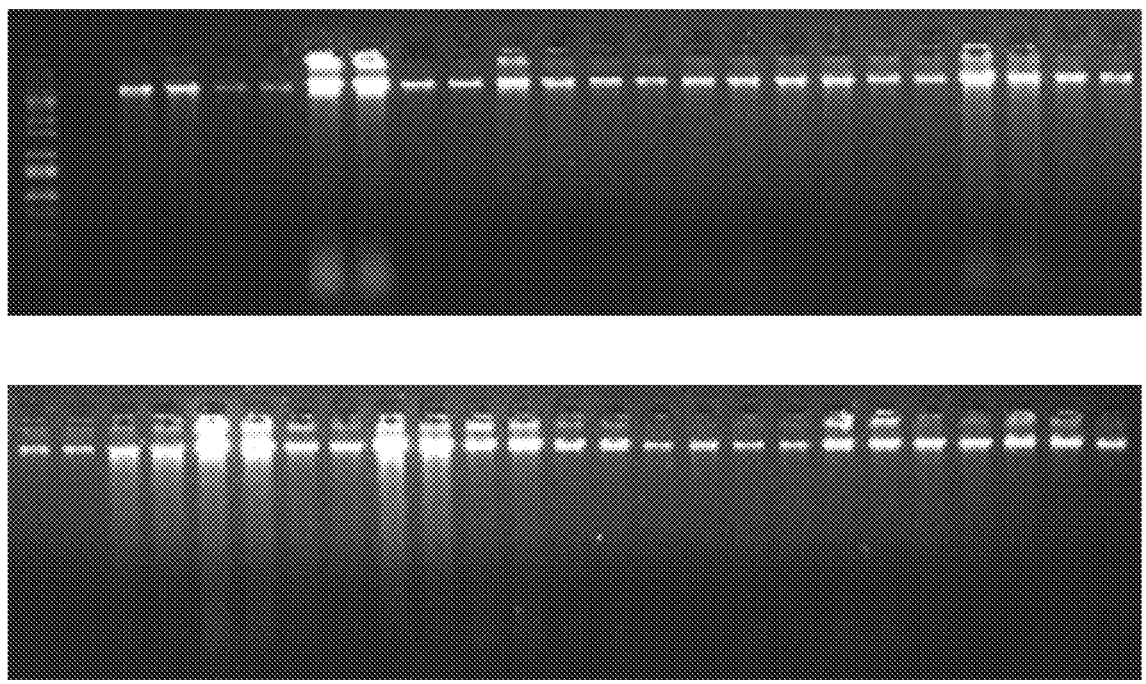
FIG. 1A is an image of a gel with high molecular weight DNA preserved using compositions according to an embodiment of the present disclosure.
Figure 1B:
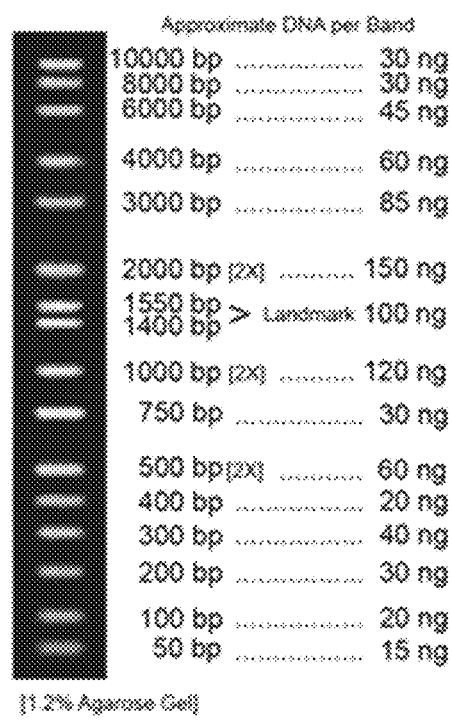
FIG. 1B is an image of a gel with Bionexus All Purpose HI-LO DNA Marker.

Before describing various embodiments of the present disclosure in detail, it is to be understood that this disclosure is not limited to the specific parameters and description of the particularly exemplified systems, methods, and/or products that may vary from one embodiment to the next. Thus, while certain embodiments of the present disclosure will be described in detail, with reference to specific features (e.g., configurations, parameters, properties, steps, components, ingredients, members, elements, parts, and/or portions, etc.), the descriptions are illustrative and are not to be construed as limiting the scope of the present disclosure and/or the claimed invention. In addition, the terminology used herein is for the purpose of describing the embodiments, and is not necessarily intended to limit the scope of the present disclosure and/or the claimed invention.

While the detailed description is separated into sections, the section headers and contents within each section are not intended to be self-contained descriptions and embodiments. Rather, the contents of each section within the detailed description are intended to be read and understood as a collective whole where elements of one section may pertain to and/or inform other sections. Accordingly, embodiments specifically disclosed within one section may also relate to and/or serve as additional and/or alternative embodiments in another section having the same and/or similar systems, devices, methods, and/or terminology.

Abbreviated List of Defined Terms

To assist in understanding the scope and content of the foregoing and forthcoming written description and appended claims, a select few terms are defined directly below. Unless defined otherwise, all technical and scientific terms used herein have the same meaning as commonly understood by one of ordinary skill in the art to which the present disclosure pertains.

As used herein, the transitional phrase "consisting essentially of" means that the scope of a claim is to be interpreted to encompass the specified materials or steps recited in the claim, "and those that do not materially affect the basic and novel characteristic(s)" of the claimed invention. See, In re Herz, 537 F.2d 549, 551-52, 190 U.S.P.Q. 461, 463 (CCPA 1976) (emphasis in the original); see also MPEP § 2111.03. Thus, the term "consisting essentially of" when used in a claim of this disclosure is not intended to be interpreted to be equivalent to "comprising."

The term "nucleic acid" as used herein refers to a naturally occurring or synthetic oligonucleotide or polynucleotide, whether DNA or RNA or DNA-RNA hybrid, single-stranded or double-stranded, sense or antisense, which is capable of hybridization to a complementary nucleic acid by Watson-Crick base-pairing. Nucleic acids of the invention can also include nucleotide analogs (e.g., BrdU, dUTP, 7-deaza-dGTP), and non-phosphodiester internucleoside linkages (e.g., peptide nucleic acid (PNA) or thiodiester linkages). In particular, nucleic acids can include, without limitation, DNA, RNA, cDNA, gDNA, ssDNA, dsDNA or any combination thereof.

The term "sample," "biological sample," and the like refers to an animal; a tissue or organ from an animal; a cell (either within a subject, taken directly from a subject, or a cell maintained in culture or from a cultured cell line); a cell lysate (or lysate fraction) or cell extract; a solution containing one or more molecules derived from a cell, cellular material, or viral material (e.g. a polypeptide or nucleic acid); or a solution containing a naturally or non-naturally occurring nucleic acid, which is or can be assayed as described herein. A sample may also be any bodily fluid or excretion that contains one or more cells, cell components, or nucleic acids, including, but not limited to cellular, nuclear, or cell-free nucleic acids.

By "bodily fluid" is meant a naturally occurring fluid, including without limitation a liquid, semi-solid, aerated liquid, liquid-gas mixture, and so forth, from an animal (e.g., human or non-human animal). Such bodily fluids can include, but are not limited to, saliva, sputum, serum, plasma, blood, urine, mucus, perspiration, tears or other ophthalmic fluids, otic fluids, puss (e.g., from a blister or sore), gastric fluids or juices, fecal fluids, pancreatic fluids or juices, semen, products of lactation or mensuration, spinal fluid, fluid bone marrow, or lymph.

By "sputum" is meant that mucoid matter contained in or discharged from the nasal or buccal cavity of a mammal. Sputum, as used herein, generally includes saliva and discharges from the respiratory passages, including the lungs.

By "saliva" is meant the secretion, or combination of secretions, from any of the salivary glands, including the parotid, submaxillary, and sublingual glands, optionally mixed with the secretion from the buccal glands.

By "mucoid" is meant any bodily fluid containing mucin.

By "mucin" is meant any mucoprotein that raises the viscosity of the medium surrounding the cells that secrete it.

As used herein, the term "about," with regard to a value, means +/−10% of the stated value or amount represented thereby. For instance, throughout the present disclosure, the term "about" is used in connection with a percent concentration or composition of a component or ingredient (e.g., in a mixture, such as a fluid or liquid mixture, aqueous mixture, solution, etc., optionally or preferably measured as a w/w percent, w/v percent, v/v percent, etc.). In such instance, the term "about" and/or the term "+/−10%" implies and/or includes +/−10% of the stated numeric value, as opposed to +/−10 percentage points of the recited percent. By way of example, where 20% w/w of a component or ingredient reflects 20 g of the component or ingredient per 100 mL of total mixture, the term "about" and/or the term "+/−10%" implies and/or includes a recited range from 18 g to 22 g (i.e., from 18% w/w to 22% w/w), not a range of 10% w/w to 30% w/w. Alternatives for so-called "about" values and/or +/−10% include +/−1%, +/−2%, +/−3%, +/−4%, +/−5%, +/−6%, +/−7%, +/−8%, or +/−9% of the stated value, each of which is contemplated as a suitable alternative to or substitute for the term "about" or the use of +/−10% herein.

As used herein, the terms "approximately" and "substantially" represent or imply an (or any) amount close to the stated amount (e.g., that still performs a desired function or achieves a (desired or expected) result). For example, the terms "approximately" and "substantially" may refer to an amount that is within, or less than, 10%, 5%, 1%, 0.1%, 0.01%, or other percent of a stated amount. As used herein, the term "substantially devoid" means (1) an undetectable or unquantifiable amount, (2) less than or below an amount generally considered by those skilled in the art to reflect a detectable or quantifiable amount, and/or (3) less than or below an amount generally considered by those skilled in the art to be functional or able to achieve a (desired or expected) result (e.g., less than 10%, 5%, 1%, 0.1%, 0.01%, or other percent).

By "Quantum satis" (also referred to as "q.s." or "qs") is meant the amount that is enough. Accordingly, a component or ingredient "qs 100%," "provided at qs 100%," or "qs to 100%" indicates that the component or ingredient is provided or included in an amount sufficient to complete the composition or to bring the total (of all components, whether recited or not) to 100%. It is noted, however, that a (final) component or ingredient "qs 100%," "provided at qs 100%," or "qs to 100%" does not indicate that the mixture consists of, consists essentially of, or only contains the components listed or recited immediately before the "qs 100%" component. In other words, "qs 100%," and similar terms, is meant to be an open-ended expression indicating the source of the remainder, whatever that remainder may be.

By "alcohol" is meant a water-miscible organic compound containing a hydroxyl group, including water-miscible mixtures of hydroxyl-containing organic compounds.

By "aqueous" is meant a medium or matter that contains 30% or more water (by volume or by weight).

By "aqueous solution" is meant a solution or suspension that contains 30% or more water by volume.

By "denaturing agent" is meant a substance that alters the natural state of that to which it is added.

By "chaotropic agent" is meant a molecule that exerts chaotropic activity. As understood by those skilled in the art, molecules that exert chaotropic activity may disrupt the hydrogen-bonding network between water molecules, thereby affecting the stability of the native state of other molecules (in the solution), mainly macromolecules (proteins, nucleic acids) by weakening the hydrophobic effect. Accordingly, molecules that exert chaotropic activity may have protein-denaturing activity (or be protein denaturants).

By "antimicrobial agent" is meant a substance or group of substances which reduces the rate of growth of an organism compared to the rate of growth of the organism in their absence. A reduction in the rate of growth of an organism may be by at least 5%, more desirably, by at least 10%, even more desirably, by at least 20%, 50%, or 75%, and most desirably, by 90% or more. The definition also extends to substances which affect the viability, virulence, or pathogenicity of an organism. An antimicrobial agent can be natural (e.g., derived from bacteria or other source), synthetic, or recombinant. An antimicrobial agent can be bacteriostatic, bactericidal or both. An antimicrobial agent is bacteriostatic if it inhibits cell division without affecting the viability of the inhibited cell. An antimicrobial agent is bactericidal if it causes cell death. Cell death is commonly detected by the absence of cell growth in liquid growth medium (e.g., absence of turbidity) or on a solid surface (e.g., absence of colony formation on agar). Those of skill in the art know that a substance or group of substances which is bacteriostatic at a given concentration may be bactericidal at a higher concentration. Certain bacteriostatic substances are not bactericidal at any concentration.

As used herein, "acetylcysteine" or "N-acetylcysteine" (NAC), includes any form of acetylcysteine, including N-acetyl-L-cysteine, N-acetyl-D-cysteine, and racemic N-acetylcysteine or a (racemic) mixture of N-acetyl-L-cysteine and N-acetyl-D-cysteine). Reference to one form of acetylcysteine supports a specific reference to any form of acetylcysteine.

As used herein, the term "composition" includes products, formulations, and mixtures, as well as devices, apparatus, assemblies, kits, and so forth. Similarly, the term "method" includes processes, procedures, steps, and so forth.

Various aspects of the present disclosure, including systems, methods, and/or products may be illustrated with reference to one or more embodiments or implementations, which are exemplary in nature. As used herein, the terms "embodiment" and "implementation" mean "serving as an example, instance, or illustration," and should not necessarily be construed as preferred or advantageous over other aspects disclosed herein. In addition, reference to an "implementation" of the present disclosure or invention includes a specific reference to one or more embodiments thereof, and vice versa, and is intended to provide illustrative examples without limiting the scope of the invention, which is indicated by the appended claims rather than by the description thereof.

As used herein, a "feature" of the present disclosure or embodiment disclosed herein refers to a property, component, ingredient, element, part, portion, (method) step, or other aspect of the subject matter at hand.

As used throughout this disclosure, the words "can" and "may" are used in a permissive sense (i.e., meaning having the potential to), rather than the mandatory sense (i.e., meaning must). Additionally, the terms "including," "having," "involving," "containing," "characterized by," variants thereof (e.g., "includes," "has," and "involves," "contains," etc.), and similar terms as used herein, including the claims, shall be inclusive and/or open-ended, shall have the same meaning as the word "comprising" and variants thereof (e.g., "comprise" and "comprises"), and do not exclude additional, un-recited elements or method steps, illustratively.

The word "or" as used herein means any one member of a particular list and also includes any combination of members of that list.

As used in this specification and the appended claims, the singular forms "a," "an" and "the" each contemplate, include, and specifically disclose both the singular and plural referents, unless the context clearly dictates otherwise. For example, reference to a "protein" contemplates and specifically discloses one, as well as two or more proteins. Similarly, use of a plural referent does not necessarily require a plurality of such referents, but contemplates, includes, and specifically discloses one, as well as two or more of such referents, unless the context clearly dictates otherwise.

It is noted that embodiments of the present disclosure can comprise one or more combinations of two or more of the features described herein. As used herein, "feature(s)" and similar terms can include, for example, compositions, ingredients, components, elements, members, parts, portions, systems, methods, configurations, parameters, properties, and so forth. Embodiments can include any of the features, options, and/or possibilities set out elsewhere in the present disclosure, including in other aspects or embodiments of the present disclosure. It is also noted that each of the foregoing, following, and/or other features described herein represents a distinct embodiment of the present disclosure. Features can also be combined and/or combinable with another one or more other features in any suitable combination and/or order, with or without one or more additional features included therewith or performed therebetween, to form unique embodiments, each of which is contemplated in the present disclosure. Such combinations of any two or more of such features represent distinct embodiments of the present disclosure. Accordingly, the present disclosure is not limited to the specific combinations of exemplary embodiments described in detail herein and disclosure of certain features relative to a specific embodiment of the present disclosure should not be construed as limiting application or inclusion of said features to the specific embodiment.

In addition, unless a feature is described as being requiring in a particular embodiment, features described in the various embodiments can be optional and may not be included in other embodiments of the present disclosure. Moreover, unless a feature is described as requiring another feature in combination therewith, any feature herein may be combined with any other feature of a same or different embodiment disclosed herein. Likewise, any steps recited in any method described herein and/or recited in the claims can be executed in any suitable order and are not necessarily limited to the order described and/or recited, unless otherwise stated (explicitly or implicitly). Such steps can, however, also be required to be performed in a particular order in certain embodiments of the present disclosure.

It will also be appreciated that where two or more values, or a range of values (e.g., less than, greater than, at least, and/or up to a certain value, and/or between two recited values) is disclosed or recited, any specific value or range of values falling within the disclosed values or range of values is likewise specifically disclosed and contemplated herein. Thus, disclosure of an illustrative measurement (e.g., length, width, thickness, etc.) that is less than or equal to about 10 units or between 0 and 10 units includes, illustratively, a specific disclosure of: (i) a measurement of 9 units, 5 units, 1 units, or any other value between 0 and 10 units, including 0 units and/or 10 units; and/or (ii) a measurement between 9 units and 1 units, between 8 units and 2 units, between 6 units and 4 units, and/or any other range of values between 0 and 10 units.

To facilitate understanding, like references (i.e., like naming of components and/or elements) have been used, where possible, to designate like elements common to different embodiments of the present disclosure. Similarly, like components, or components with like functions, will be provided with similar reference designations, where possible. Specific language will be used herein to describe the exemplary embodiments. Nevertheless it will be understood that no limitation of the scope of the disclosure is thereby intended. Rather, it is to be understood that the language used to describe the exemplary embodiments is illustrative only and is not to be construed as limiting the scope of the disclosure (unless such language is expressly described herein as essential).

Illustrative Embodiments

The following description of embodiments includes disclosure that is relevant to one or more embodiments of the present disclosure. Accordingly, some embodiments can include features disclosed in the following examples without departing from the scope of the present disclosure. In other words, features disclosed in the following examples can be included and/or incorporated into any one or more of the embodiments disclosed herein.

Compositions

Some embodiments of the present disclosure include a composition. The compositions can render sputum or saliva as a viable source of nucleic acids for purification and analysis. The compositions provide the advantageous properties of chemical stabilization of nucleic acids and the inhibition of nucleases, including deoxyribonucleases, and microbial growth. Chemical stabilization of the nucleic acids in a saliva sample can be achieved through the use of buffers, acids, chelating agents, mucolytic agents, chaotropic agents, surfactants, and alcohol.

The compositions of the present disclosure, when mixed with a biological sample, e.g., mucin-containing bodily fluid, can preserve the nucleic acids at room temperature under ambient conditions for extended periods of time. Samples can also be refrigerated, but freezing of the samples before nucleic acid recovery and purification is not required. The properties of certain composition of the present disclosure are that it (a) chemically stabilizes nucleic acids, (b) inhibits nucleases that may be present in the saliva, and (c) is compatible with proteolytic enzymes and other reagents used to purify/amplify oligo- or polynucleotides.

Carriers

In at least one embodiment, the composition can include a carrier. Preferably, the carrier can be a liquid carrier or solvent, more preferably an aqueous carrier or solvent, still more preferably water. Most preferably, the carrier can be or comprise purified, filtered (e.g., 0.2 micron filtered), distilled, and/or deionized water. Accordingly, the composition can include a carrier. The carrier can be or comprise water, such as filtered water, purified water, distilled water, or deionized water.

In some embodiments, the composition can include a carrier qs to 100%. In some embodiments, the composition can include 10-60%, preferably 15-55%, more preferably 20-50%, still more preferably 25-45% still more preferably 28-40%, still more preferably 30-35%, still more preferably 31-34%, still more preferably 32-33% carrier, w/w (or any value or range of values therebetween). Most preferably, the composition can include (about) 32.602% water, w/w.

Chaotropic Agents

The composition can include one or more chaotropic agents. In one or more embodiments, the chaotropic agent(s) can be a protein denaturant. In some embodiments, the chaotropic agent can be selected from the group consisting of: guanidinium chloride and/or guanidinium thiocyanate. Accordingly, in at least one embodiment, the composition can include a chaotropic agent. Preferably, the chaotropic agent can be or comprise guanidine (or guanidinium) or a suitable salt thereof. More preferably, the chaotropic agent can be or comprise guanidine thiocyanate. In at least one embodiment, the chaotropic agent can be or comprise thiocyanate. In at least one embodiment, the chaotropic agent can be or comprise guanidine isothiocyanate, guanidine chloride, guanidine hydrochloride, guanidinium iodide, and so forth.

In some embodiments, the chaotropic agent can be in, have, comprise, or be provided in a dry, solid, powdered, anhydrous, and/or granular form. In some embodiments, the chaotropic agent can have a purity of at least, up to, and/or about 90%, 95%, 96%, 97%, 98%, 99%, 99.1%, 99.2%. 99.3%, 99.4%, 99.5%, 99.6%, 99.7%, 99.8%, or 99.9% (as measured by a suitable material assay, such as CoA). In some embodiments, the chaotropic agent can comprise or be (provided) in the form of a stock solution (e.g., in water) having any suitable concentration. In some embodiments, the chaotropic agent can have a purity substantially corresponding to the concentration of the chaotropic agent in solution (as measured by a suitable material assay, such as CoA).

In some embodiments, the composition can include 20-50%, preferably 25-49%, more preferably 30-48% still more preferably 35-47%, still more preferably 40-46%, still more preferably 42-45%, still more preferably 43-44% of the chaotropic agent (e.g., guanidine thiocyanate), w/w, or any value or range of values therebetween. Most preferably, the composition can include (about) 43.92% guanidine thiocyanate, w/w. The chaotropic agent (e.g., guanidine thiocyanate) can be included in the composition at about 43.92% w/w, or in a range of about 35% to about 50%, preferably about 40% to about 46%, more preferably about 42% to about 45%, still more preferably about 43% to about 44%, w/w.

Buffering Agents

The composition can include one or more buffering agents (or buffers, pH buffers, etc.). Examples of buffering agents include, but are not limited to tris(hydroxymethyl)aminomethane (also known as Tris; Tris base, 2-Amino-2-(hydroxymethyl)-1,3-propanediol, THAM, Trometamol) or a suitable formulation thereof (e.g., tris(hydroxymethyl)aminomethane hydrochloride, or Tris-HCl,), Trizma® base (e.g., Tris 40% (w/w) stock solution in water), HEPES, BES, MOPS, HEPES, TAE, TBE, phosphate buffer, sodium borate buffer, sodium cacodylate buffer, and so forth. Preferably, the buffering agent can be or comprise tris(hydroxymethyl) aminomethane (Tris). More preferably, the buffering agent can be or comprise Tris-HCl. Most preferably, the buffering agent can be or comprise Trizma® base.

In some embodiments, the buffering agent can be in, have, comprise, or be provided in a dry, solid, powdered, anhydrous, and/or granular form. In some embodiments, the buffering agent can have a purity of at least, up to, and/or about 90%, 95%, 96%, 97%, 98%, 99%, 99.1%, 99.2%. 99.3%, 99.4%, 99.5%, 99.6%, 99.7%, 99.8%, or 99.9% (as measured by a suitable material assay, such as CoA). In some embodiments, the buffering agent can comprise or be (provided) in the form of a stock solution (e.g., in water) having any suitable concentration (e.g., Tris ~40% (w/w) stock solution in water). In some embodiments, the buffering agent can have a purity substantially corresponding to the concentration of the buffering agent in solution (as measured by a suitable material assay, such as CoA).

The buffering agent can be included in the composition at about 2.65% % w/w, or in a range of about 0.1% to about 5%, preferably about 0.5% to about 4.5%, more preferably about 0.75% to about 4%, still more preferably about 1% to about 3.5%, still more preferably about 1.5% to about 3.25%, still more preferably about 2% to about 3%, still more preferably about 2.5% to about 2.8%, w/w. In some embodiments, the composition can include 1-5%, preferably 1.25-4.5%, more preferably 1.5-4% still more preferably 1.75-3.75%, still more preferably 2-3.5%, still more preferably 2.25-3%, still more preferably 2.5-2.75% of the buffering agent (e.g., Tris), w/w, or any value or range of values therebetween. Most preferably, the composition can include (about) 2.65% Tris, w/w.

Chelating Agents

In at least one embodiment, the composition can include a chelating agent (or chelator). Preferably, the chelating agent can be or comprise ethyenediaminetetraacetic acid (EDTA) or suitable salt and/or hydrate thereof. More preferably, the chelating agent can be or comprise, or be provided as EDTA disodium salt. Still more preferably, the chelating agent can be or comprise, or be provided as EDTA disodium (salt) dihydrate. In at least one embodiment, the chelating agent can be or comprise ethylene glycol-bis(β-aminoethyl ether)-N,N,N',N'-tetraacetic acid (EGTA), nitrilotriacetic acid (NTA), an ethylenediamine (or 1,2-diaminoethane), and so forth. In some embodiments, the chelating agent comprises, includes, or is provide with a counter ion (e.g., sodium). In at least one embodiment, the chelating agent comprises, includes, or is provide as a hydrate (e.g., dihydrate).

The composition can include one or more chelating agents. The chelating agent of the composition can be selected from the group consisting of: ethylenediamine tetraacetic acid (EDTA), cyclohexane diaminetetraacetate (CDTA), diethylenetriamine pentaacetic acid (DTPA), tetraazacyclododecanetetraacetic acid (DOTA), tetraazacyclotetradecanetetraacetic acid (TETA), desferrioximine, nitrilotriacetic acid (NTA), an ethylenediamine (or 1,2-diaminoethane), or respective chelator analogs, salts, and/or hydrates thereof. Preferably, the chelating agent can be or comprise EDTA (e.g., as EDTA disodium salt, preferably as EDTA disodium (salt) dihydrate). In some embodiments, the chelating agent comprises, includes, or is provide with a counter ion (e.g., sodium). In at least one embodiment, the chelating agent comprises, includes, or is provide as a hydrate (e.g., dihydrate).

In some embodiments, the chelating agent can be in, have, comprise, or be provided in a dry, solid, powdered, anhydrous, and/or granular form. In some embodiments, the chelating agent can have a purity of at least, up to, and/or about 90%, 95%, 96%, 97%, 98%, 99%, 99.1%, 99.2%. 99.3%, 99.4%, 99.5%, 99.6%, 99.7%, 99.8%, or 99.9% (as measured by a suitable material assay, such as CoA). In some embodiments, the chelating agent can comprise or be (provided) in the form of a stock solution (e.g., in water) having any suitable concentration. In some embodiments, the chelating agent can have a purity substantially corresponding to the concentration of the chelating agent in solution (as measured by a suitable material assay, such as CoA).

The chelating agent (e.g., EDTA) can be included in the composition at about 0.81% w/w, or in a range of about 0.05% to about 2.5%, preferably about 0.1% to about 2%, more preferably about 0.5% to about 1%, still more preferably about 0.75% to about 0.9%, w/w. In some embodiments, the composition can include 0.05-2.5%, preferably 0.1-2.25%, more preferably 0.25-2% still more preferably 0.5-1.75%, still more preferably 0.6-1.5%, still more preferably 0.7-1.25%, still more preferably 0.75-1% of the chelating agent (e.g., EDTA), w/w, or any value or range of values therebetween. Most preferably, the composition can include (about) 0.81% EDTA or EDTA disodium (salt) dihydrate, w/w.

Surfactants

In at least one embodiment, the composition can include a surfactant or detergent. Preferably, the surfactant can be or comprise a lauroyl sarcosinate. More preferably, the surfactant can be or comprise sodium lauroyl sarcosinate (SLS). In at least one embodiment, the surfactant can be or comprise one or more components selected from the group consisting of sodium dodecyl sulfate (SDS), polysorbates (Tween™), lauryl dimethyl amine oxide, cetyltrimethylammonium bromide (CTAB), polyethoxylated alcohols, polyoxyethylene sorbitan, octoxynol (Triton X100™), N,N-dimethyldodecylamine-N-oxide, hexadecyltrimethylammonium bromide (HTAB), polyoxyl 10 lauryl ether, Bile salts (sodium deoxycholate, sodium cholate), polyoxyl castor oil (Cremophor™), nonylphenol ethoxylate (Tergitol™), cyclodextrins, lecithin, methylbenzethonium chloride (Hyamine™), and so forth. The composition can include a surfactant or detergent, such as urea, perchlorate, (sodium) dodecyl sulfate (SDS), and/or (sodium) lauroyl sarcosinate (SLS), preferably sodium lauroyl sarcosinate (SLS). In some embodiments, SLS can be preferable over SDS or other (less soluble) surfactants.

In some embodiments, the surfactant can be in, have, comprise, or be provided in a dry, solid, powdered, anhydrous, and/or granular form. In some embodiments, the surfactant can have a purity of at least, up to, and/or about 90%, 95%, 96%, 97%, 98%, 99%, 99.1%, 99.2%. 99.3%, 99.4%, 99.5%, 99.6%, 99.7%, 99.8%, or 99.9% (as measured by a suitable material assay, such as CoA). In some embodiments, the surfactant can comprise or be (provided) in the form of a stock solution (e.g., in water) having any suitable concentration (e.g., about 10%, 15%, 20%, 25%, 28%, 29%, 30%, 32%, 35%, 40%, or 45%, w/w, aqueous solution (e.g., in water). In some embodiments, the surfactant can have a purity substantially corresponding to the concentration of the surfactant in solution (e.g., about 30%, w/w) (as measured by a suitable material assay, such as CoA).

In some embodiments, the surfactant (e.g., SLS) can be included in the composition at about 0.279%, w/w. In some embodiments, the surfactant can be included in the composition in a range of about 0.01% to about 5%, w/w, preferably about 0.025% to about 2.5%, w/w, more preferably about 0.05% to about 2%, w/w, still more preferably about 0.075% to about 1.5%, w/w, still more preferably about 0.1% to about 1%, w/w, still more preferably about 0.15% to about 0.5%, w/w, still more preferably about 0.2% to about 0.4%, w/w, still more preferably about 0.25% to about 0.3%, w/w. Some embodiments include 0.01% to 5%, w/w, preferably 0.025% to 2.5%, w/w, more preferably 0.05% to 2%, w/w, still more preferably 0.075% to 1.5%, w/w, still more preferably 0.1% to 1%, w/w, still more preferably 0.15% to 0.5%, w/w, still more preferably 0.2% to 0.4%, w/w, still more preferably 0.25% to 0.3%, w/w, most preferably 0.279%, w/w, surfactant or SLS. In at least one embodiment, the surfactant (e.g., SLS) can be included in the composition at about 0.93% w/w, of a ~30% stock (aqueous) solution, or equivalent thereof.

Alcohols

In at least one embodiment, the composition can include an alcohol. Preferably, the alcohol can be or comprise ethanol. More preferably, the alcohol can be or comprise a mixture of ethanol and one or more additional chemicals or components. In at least one embodiment, the one or more additional chemicals or components can be or comprise isopropanol. Still more preferably, the alcohol can be or comprise a mixture of ethanol and isopropanol. In at least one embodiment, the one or more additional chemicals or components can be or comprise methanol, propanol, butanol, isobutanol, and so forth. In at least one embodiment, the alcohol can be or comprise a specially denatured alcohol (SDA). More preferably, the alcohol can be or comprise SDA 3C, as known to those skilled in the art to comprise a mixture of about 95% ethanol v/v and about 5% isopropanol v/v. The composition can include an alcohol, such as ethanol, methanol, propanol, and/or isopropanol, preferably a specially denatured alcohol (SDA) or a mixture of ethanol and another alcohol, such as methanol, n-propanol, isopropanol, n-butanol, trifluoroethanol, phenol, or 2,6-di-tert-butyl-4-methylphenol, more preferably a mixture of ethanol and isopropanol, still more preferably a mixture of ethanol and one or more additional chemicals or components, such as isopropanol.

In some embodiments, the surfactant can be in, have, comprise, or be provided in a dry, solid, powdered, anhydrous, and/or granular form. In some embodiments, the alcohol can be in, have, comprise, or be provided in a liquid, aqueous, and/or solution form. In some embodiments, the alcohol can comprise or be (provided) in the form of a stock solution (e.g., in water) having any suitable concentration of alcohol (e.g., in water). In some embodiments, the alcohol can be substantially pure, or a mixture of substantially pure alcohols. In some embodiments, the alcohol can have a purity of at least, up to, and/or about 90%, 95%, 96%, 97%, 98%, 99%, 99.1%, 99.2%. 99.3%, 99.4%, 99.5%, 99.6%, 99.7%, 99.8%, or 99.9% (or pure ethyl alcohol, 200 proof) (as measured by a suitable material assay, such as CoA).

In some embodiments, the alcohol can be or comprise a mixture or stock solution of or comprising about 95% v/v ethanol and about 5% v/v isopropanol. In some embodiments, the alcohol can be or comprise a mixture or stock solution of or comprising 90-99% v/v ethanol and about 1-10% v/v isopropanol. In certain embodiments, the alcohol can comprise a mixture of 50-99% ethanol v/v and 1-50% isopropanol v/v. More preferably, the alcohol can comprise a mixture of 60-98% ethanol v/v and 2-40% isopropanol v/v. Still more preferably, the alcohol can comprise a mixture of 75-97% ethanol v/v and 3-25% isopropanol v/v. Still more preferably, the alcohol can comprise a mixture of 80-96% ethanol v/v and 4-20% isopropanol v/v. Still more preferably, the alcohol can comprise a mixture of 85-95% ethanol v/v and 5-15% isopropanol v/v. Still more preferably, the alcohol can comprise a mixture of 90-95% ethanol v/v and 5-10% isopropanol v/v. Still more preferably, the alcohol can comprise a mixture of 92-95% ethanol v/v and 5-8% isopropanol v/v. Still more preferably, the alcohol can comprise a mixture of 95% ethanol v/v and 5% isopropanol v/v. Most preferably, the alcohol can be or comprise SDA 3C.

The alcohol (e.g., SDA 3C) can be included in the composition at about 17.73% w/w, or in a range of about 10% to about 25%, preferably about 12% to about 22%, more preferably about 15% to about 20%, still more preferably about 16% to about 19%, still more preferably about 17% to about 18%, w/w. In some embodiments, the amount of alcohol included in the composition can be less (e.g., about 20%, 25%, 30%, 35%, 40%, 45%, 50%, 55%, or 60% less) than typical, traditional, or existing nucleic acid preservation solutions (e.g., making the composition more amendable to shipping or transport). In some embodiments, the composition can include 5-25%, preferably 10-22%, more preferably 12-20% still more preferably 15-19%, still more preferably 16-18.5%, still more preferably 17-18.25%, still more preferably 17.5-18% alcohol, w/w, or any value or range of values therebetween.

Preferably, the alcohol comprises a mixture of ethanol and one or more additional chemicals or components, such as isopropanol, more preferably a mixture of about 95% ethanol, v/v and about 5% isopropanol, v/v. Still more preferably, the alcohol is a specially denatured alcohol (SDA), still more preferably SDA 3C (i.e., a mixture of ~95% ethanol and ~5% isopropanol, v/v). Most preferably, the composition can include (about) 17.73% SDA 3C, w/w. In some embodiments, the alcohol (e.g., SDA 3C) can be included in the composition at about 16.84% w/w, ethanol or in a range of about 10% to about 25%, preferably about 12% to about 22%, more preferably about 15% to about 20%, still more preferably about 16% to about 18%, still more preferably about 16.5% to about 17%, w/w, ethanol, and about 0.89% w/w, isopropanol or in a range of about 0.05% to about 2.5%, preferably about 0.1% to about 2%, more preferably about 0.5% to about 1.5%, still more preferably about 0.75% to about 1.25%, still more preferably about 0.8% to about 1%, w/w, isopropanol.

In some embodiments, the amount of alcohol included in the composition can be less (e.g., about 50% less) than typical, traditional, or existing nucleic acid preservation solutions (e.g., making the composition more amendable to shipping or transport).

Acids

In at least one embodiment, the composition can include an acid. Preferably, the acid can be or comprise hydrochloric acid (HCl). In at least one embodiment, the acid can be or comprise hydrobromic acid (HBr), perchloric acid (HClO4), nitric acid (HNO3), or sulfuric acid (H2SO4). In at least one embodiment, the acid can be or comprise carbonic acid (H2CO3) or acetic acid (CH3COOH). In at least one embodiment, the acid can be or comprise phosphoric acid (H3PO4), boric acid (H3BO3), or Emerald Safe acid (ESA), and so forth.

In some embodiments, the acid can be in, have, comprise, or be provided in a dry, solid, powdered, anhydrous, and/or granular form. In some embodiments, the acid can have a purity of at least, up to, and/or about 90%, 95%, 96%, 97%, 98%, 99%, 99.1%, 99.2%. 99.3%, 99.4%, 99.5%, 99.6%, 99.7%, 99.8%, or 99.9% (as measured by a suitable material assay, such as CoA). In some embodiments, the acid can comprise or be (provided) in the form of a stock solution (e.g., in water) having any suitable concentration (e.g., about 10%, 15%, 20%, 25%, 30%, 32%, 35%, 37%, 38%, 40%, or 45%, w/w, aqueous solution (e.g., in water). In some embodiments, the acid can have a purity substantially corresponding to the concentration of the acid in solution (e.g., about 37%, w/w) (as measured by a suitable material assay, such as CoA).

In some embodiments, the composition can include acid (e.g., hydrochloric acid), qs to pH about 8.0, or pH 7.5-9.5, pH 6.5-9.5, pH 7-9, pH 7.2-8.8, pH 7.4-8.6, pH 7.5-8.5, pH 7.6-8.4, or pH 7.8-8.2 (or any value or range of values therebetween). In some embodiments, the pH of the composition can be greater than about 5 and less than about 12, preferably within a pH range of about 6 to about 11, more preferably within a pH range of about 6 to about 10, still more preferably within a pH range of about 7 to about 9, still more preferably within a pH range of about 7.5 to about 8.5, and most preferably, with a pH of about 8.0.

In some embodiments, the acid (e.g., HCl) can be included in the composition at about 0.4% w/w, or in a range of about 0.01% to about 5%, preferably about 0.025% to about 2.5%, more preferably about 0.05% to about 2%, preferably about 0.1% to about 1.5%, more preferably about 0.25% to about 1%, more preferably about 0.5% to about 0.75%, more preferably about 0.3% to about 0.5%, w/w. In some embodiments, the composition can include 0.005-5%, preferably 0.01-2.5%, more preferably 0.025-1.5%, still more preferably 0.05-1% still more preferably 0.1-0.75%, still more preferably 0.25-0.5% acid (e.g., hydrochloric acid), w/w. In at least one embodiment, the acid (e.g., HCl) can be included in the composition at about 1.08%, w/w, of a ~37%, w/w, or ~12M stock (aqueous) solution, or equivalent thereof. Most preferably, the composition can include (about) 1.08% hydrochloric acid 37%, w/w, or equivalent thereof, or hydrochloric acid qs to pH (about) 8.0.

Without being bound to any theory, it is noted, and those skilled in the art will appreciate that different acids have different "strengths" or the ability or tendency of the acid to lose a proton (H+). A strong acid is one that completely ionizes (dissociates) in a solution (provided there is sufficient solvent). In water, for example, one mole of a strong acid HA dissolves yielding one mole of H+ (as hydronium ion H3O+ and higher aggregates) and one mole of the conjugate base, A-. Essentially, none of the non-ionized acid HA remains. Some examples of strong acids are hydrochloric acid (HCl), hydroiodic acid (HI), hydrobromic acid (HBr), perchloric acid (HClO4), nitric acid (HNO3) and sulfuric acid (H2SO4). In aqueous solution, each of these essentially ionizes 100%. In contrast, a weak acid only partially dissociates. Examples in water include carbonic acid (H2CO3) and acetic acid (CH3COOH). At equilibrium, both the acid and the conjugate base are present in solution. Stronger acids have a larger acid dissociation constant (Ka) and a smaller logarithmic constant (pKa=-log Ka) than weaker acids. The stronger an acid is, the more easily it loses a proton, H+. Two key factors that contribute to the ease of deprotonation are the polarity of the H—A bond and the size of atom A, which determines the strength of the H—A bond. Acid strengths also depend on the stability of the conjugate base.

In light of the foregoing, the w/w amount of each acid necessary to bring the pH of the composition to a desired level is different. For instance, while (about) 1.08% hydrochloric acid 37%, w/w (in water), may be sufficient to bring certain embodiments of the present disclosure to pH (about) 8.0, 1.08% acetic acid 37%, w/w (in water), may be too weak to bring a similar embodiment to pH (about) 8.0, 1.08% sulfuric acid 37%, w/w (in water), may be too strong to bring the embodiment to pH (about) 8.0, 1.08% nitric acid 37%, w/w (in water), may oxidize the alcohol, and so forth. Without being bound to any theory, even those of ordinary skill in the art may not, with further experimentation, be able to determine which acids are suitable in one or more embodiments of the present disclosure.

Mucolytic Agents

In at least one embodiment, the composition can include a mucolytic agent. In one or more embodiments, the mucolytic agent can be or comprise a reducing agent. Preferably, the mucolytic agent can be or comprise an acetylcysteine (i.e., N-acetylcysteine (NAC), including N-acetyl-L-cysteine, N-acetyl-D-cysteine, and racemic N-acetylcysteine or a (racemic) mixture of N-acetyl-L-cysteine and N-acetyl-D-cysteine). More preferably, the mucolytic agent can be or comprise N-Acetyl-L-cysteine. In at least one embodiment, the mucolytic agent can be or comprise N-acetylcysteine (N-acetyl-L-cysteine), ascorbic acid, dithionite, erythiorbate, cysteine, glutathione, dithiothreitol, 2-mercaptoethanol, dierythritol, a resin-supported thiol, a resin-supported phosphine, vitamin E, and/or trolox, or salts thereof, sodium citrate, potassium citrate, potassium iodide, ammonium chloride, guaiphenesin (or guaifenesin), Tolu balsam, Vasaka, ambroxol, carbocisteine, erdosteine, mecysteine, dornase alfa, and so forth. The composition can include one or more mucolytic agent. Preferably, the mucolytic agent is ascorbic acid, erythiorbate, N-acetylcysteine, dithiothreitol, or 2-mercaptoethanol, and most preferably, the mucolytic agent is N-acetylcysteine.

In one or more embodiments, the composition does not contain ascorbic acid, dithionite, erythiorbate, dithiothreitol, 2-mercaptoethanol, dierythritol, a resin-supported thiol, a resin-supported phosphine, vitamin E, trolox, and/or salts thereof. At least one embodiment is (substantially) devoid of ascorbic acid, dithionite, erythiorbate, dithiothreitol, 2-mercaptoethanol, dierythritol, a resin-supported thiol, a resin-supported phosphine, vitamin E, trolox, and/or salts thereof. At least one embodiment is (substantially) devoid of a mucolytic agent besides N-acetyl-L-cysteine.

In some embodiments, the mucolytic agent can be in, have, comprise, or be provided in a dry, solid, powdered, anhydrous, and/or granular form. In some embodiments, the mucolytic agent can have a purity of at least, up to, and/or about 90%, 95%, 96%, 97%, 98%, 99%, 99.1%, 99.2%. 99.3%, 99.4%, 99.5%, 99.6%, 99.7%, 99.8%, or 99.9% (as measured by a suitable material assay, such as CoA). In some embodiments, the mucolytic agent can comprise or be (provided) in the form of a stock solution (e.g., in water) having any suitable concentration. In some embodiments, the mucolytic agent can have a purity substantially corresponding to the concentration of the mucolytic agent in solution (as measured by a suitable material assay, such as CoA).

The mucolytic agent (e.g., N-acetylcysteine) can be included in the composition at about 0.093% w/w, or in a range of about 0.01% to about 0.5%, preferably about 0.025% to about 0.25%, more preferably about 0.05% to about 0.2%, still more preferably about 0.075% to about 0.15%, still more preferably about 0.08% to about 0.1%, w/w.

In some embodiments, the composition can include 0.005-0.25%, preferably 0.005-0.2%, more preferably 0.01-0.2%, still more preferably 0.025-0.175% still more preferably 0.05-0.165%, still more preferably 0.075-0.15%, still more preferably 0.08-0.125%, still more preferably 0.09-0.1% of the mucolytic agent (e.g., N-acetyl-L-cysteine), w/w, or any value or range of values therebetween. Most preferably, the composition can include (about) 0.093% N-acetyl-L-cysteine, w/w.

Visual Indicators

At least one embodiment can include a visual indicator. Preferably, the visual indicator can be or comprise a coloring agent. More preferably, the visual indicator can be or comprise a dye or colored dye. Still more preferably, the visual indicator can be or comprise a blue dye. Most preferably, the visual indicator can be or comprise FD&C Blue No. 1. The composition can include a visual indicator, preferably a coloring agent, more preferably a colored dye, still more preferably a blue dye, still more preferably FD&C Blue No. 1.

In some embodiments, the visual indicator can be in, have, comprise, or be provided in a dry, solid, powdered, anhydrous, and/or granular form. In some embodiments, the visual indicator can have a purity of at least, up to, and/or about 80%, 85%, 86%, 87%, 88%, 89%, 90%, 91%, 92%, 93%, 94%, 95%, 96%, 97%, 98%, 99%, 99.1%, 99.2%. 99.3%, 99.4%, 99.5%, 99.6%, 99.7%, 99.8%, or 99.9% (as measured by a suitable material assay, such as CoA). In some embodiments, the visual indicator can comprise or be (provided) in the form of a stock (solution (e.g., in water))

having any suitable concentration (e.g., about 0.01%, 0.05%, 0.075%, 0.1%, 0.125%, 0.15%, 0.175%, 0.2%, 0.25%, 0.3%, or 0.5%, w/w, aqueous solution (e.g., in water). In some embodiments, stock solution can be made using the dry, solid, powdered, anhydrous, and/or granular material. In some embodiments, the visual indicator can have a purity substantially corresponding to the concentration of the acid in solution (e.g., about 0.2%, w/w) (as measured by a suitable material assay, such as CoA).

The visual indicator (e.g., FD&C Blue No. 1) can be included in the composition in any visually suitable amount, such as about 0.00037% w/w, or in a range of about 0.00005% to about 0.001%, preferably about 0.0001% to about 0.00075%, more preferably about 0.0002% to about 0.0005%, w/w, still more preferably about 0.0003% to about 0.0004%, w/w. In some embodiments, the composition can include a visible (or visibly suitable) amount of a visual indicator, preferably a coloring agent, more preferably a colored dye, still more preferably a blue dye, still more preferably FD&C Blue No. 1. Most preferably, the composition can include (about) 0.00037% w/w of FD&C Blue No. 1.

In at least one embodiment, the visual indicator (e.g., FD&C Blue No. 1) can be added to the composition as a concentrate. The concentrate can be an aqueous or water-based concentrate in some embodiments. In some embodiments, the composition can include 0.01-2.5%, w/w, of a 0.01-5%, w/w (in water) visual indicator concentrate. Preferably, the composition can include 0.05-1%, w/w, of a 0.05-1%, w/w (in water) visual indicator concentrate. More preferably, the composition can include 0.075-0.5%, w/w, of a 0.075-0.5%, w/w (in water) visual indicator concentrate. Still more preferably, the composition can include 0.1-0.25%, w/w, of a 0.1-0.25%, w/w (in water) visual indicator concentrate. Still more preferably, the composition can include (about) 0.185% w/w of (about) 0.2% w/w (in water) visual indicator concentrate. In at least one embodiment, the visual indicator (e.g., FD&C Blue No. 1) can be included in the composition at about 0.185%, w/w, of a ~0.2% stock (aqueous) solution, or equivalent thereof. Most preferably, the composition can include (about) 0.185% w/w of (about) 0.2% w/w (in water) FD&C Blue No. 1 concentrate.

Antimicrobials

In some embodiments, the composition can include an antimicrobial agent. In some embodiments, one or more of the foregoing components can exhibit antimicrobial activity. For instance, the alcohol, chaotropic agent, surfactant, and/or mucolytic agent can be antimicrobial or exhibit antimicrobial activity in some embodiments. Accordingly, certain embodiments need not include a separate antimicrobial (e.g., bactericidal and/or bacteriostatic) agent. In one or more embodiments, the antimicrobial properties of alcohol (e.g., SDA 3C) persist even at the lower concentrations in which the alcohol is provided in said embodiment(s) of the present disclosure (e.g., about 17.73%, w/w, or 5-25%, 10-22%, 10-20% 15-19%, 16-18.5%, 17-18.25%, or 17.5-18%, w/w, or any value or range of values therebetween).

Ribonuclease Inhibitors

Some embodiments include a ribonuclease inhibitor, or inhibitor of ribonuclease, such as heparin, heparan sulfate, oligo (vinylsulfonic acid), poly(vinylsulfonic acid), oligo (vinylphosphonic acid), and poly(vinylsulfonic acid), or salts thereof. In certain (e.g., preferred) embodiments, the composition does not include a ribonuclease inhibitor or inhibitor of ribonuclease, or is (substantially) devoid of one or more (e.g., any) ribonuclease inhibitor or inhibitor of ribonuclease (e.g., other than a chaotropic agent, such as guanidine thiocyanate, which may have intrinsic RNAse inhibitory activity). Accordingly, at least one embodiment is (substantially) devoid of one or more (any) ribonuclease inhibitor, or inhibitor of ribonuclease. One or more embodiments are (substantially) devoid of any ribonuclease inhibitor, or inhibitor of ribonuclease (e.g., other than a chaotropic agent, such as guanidine thiocyanate).

Proteases

Some embodiments include a protease. In certain (e.g., preferred) embodiments, the composition does not include a protease, or is (substantially) devoid of one or more (e.g., any) protease. Accordingly, at least one embodiment is (substantially) devoid of one or more (any) protease. Without being bound to any theory, a protease (or proteolytic enzyme, peptidase or proteinase) is a type of enzyme that breaks one or more peptide bonds through hydrolysis, thereby converting proteins into smaller protein fragments (or peptides) or individual protein subunits (or amino acids).

Protein Denaturants

Some embodiments include one or more protein denaturants. For instance, in at least one embodiment, the (i) chaotropic agent can be, comprise, or function as a protein denaturant (or denature proteins or have or exhibit protein denaturation activity). In at least one embodiment, the (ii) surfactant/detergent can be, comprise, or function as a protein denaturant (or denature proteins or have or exhibit protein denaturation activity). In at least one embodiment, the (iii) alcohol can be, comprise, or function as a protein denaturant (or denature proteins or have or exhibit protein denaturation activity). In at least one embodiment, the (iv) mucolytic agent can be, comprise, or function as a protein denaturant (or denature proteins or have or exhibit protein denaturation activity), such as when the protein(s) contain accessible disulfide bonds or bridges. In some embodiments, two or more of the (i) chaotropic agent, (ii) surfactant/detergent, (iii) alcohol, and (iv) mucolytic agent can be, comprise, or function as a protein denaturant (or denature proteins or have or exhibit protein denaturation activity). In some embodiments, each or all of the (i) chaotropic agent, (ii) surfactant/detergent, (iii) alcohol, and (iv) mucolytic agent can be, comprise, or function as a protein denaturant (or denature proteins or have or exhibit protein denaturation activity).

Without being bound to any theory, the protein denaturation activity of one or more of the foregoing components or ingredients can be concentration and/or time dependent.

Formulations

An embodiment of the present disclosure includes a nucleic acid preservation composition (or formulation), comprising a carrier, a chaotropic agent, a buffering agent, a chelating agent, a surfactant, an alcohol, an acid, and a mucolytic agent. An embodiment further includes an optional visual indicator. An embodiment can include 20-50% chaotropic agent, w/w, 1-5% buffering agent, w/w, 0.05-2.5% chelating agent, w/w, 0.05-2.5% surfactant, w/w, 5-25% alcohol, w/w, 0.005-0.25% mucolytic agent, w/w, acid qs to pH 6.5-9.5, and the carrier qs to 100%. An embodiment can further include 0.005-2.5%, w/w, visual indicator.

In at least one embodiment, the composition includes about 43.92% w/w of the chaotropic agent, about 2.65% w/w of the buffering agent, about 0.81% w/w of the chelating agent, about 0.279% w/w of the surfactant, about 17.73% w/w of the alcohol, about 0.093% w/w of the mucolytic agent; the acid qs to a pH of about 8.0 (e.g., about 1.08% of a 37% acid solution, or equivalent thereof), and the carrier qs to 100%. The composition can include about 0.00037% w/w of the visual indicator.

In some embodiments, the carrier can be or comprise an aqueous carrier, such as water, preferably filtered, purified, distilled, and/or deionized water. In some embodiments, the chaotropic agent can be or comprise guanidine and/or thiocyanate, preferably guanidine thiocyanate. In some embodiments, the buffering agent can be or comprise tris(hydroxymethyl)aminomethane (Tris), preferably Tris-HCl, more preferably Trizma® base. In some embodiments, the chelating agent can be or comprise ethyenediaminetetraacetic acid (EDTA), preferably EDTA disodium (salt) dihydrate. In some embodiments, the surfactant can be or comprise sodium lauroyl sarcosinate (SLS). In some embodiments, the alcohol can be or comprise a specially denatured alcohol (SDA) or a mixture of ethanol and isopropanol, preferably a mixture of about 95% ethanol, v/v and about 5% isopropanol, v/v, or SDA 3C. In some embodiments, the acid can be or comprise hydrochloric acid. In some embodiments, the mucolytic agent can be or comprise N-acetyl-L-cysteine.

An embodiment of the present disclosure includes a nucleic acid stabilization and/or preservation composition, comprising about 43.92% chaotropic agent (e.g., guanidine thiocyanate), w/w, about 2.65% buffering agent (e.g., Tris), w/w, about 0.81% chelating agent (e.g., EDTA or EDTA disodium (salt) dihydrate), w/w, about 0.279% surfactant (e.g., SLS), w/w, about 17.73% alcohol (e.g., SDA 3C), w/w, about 0.093% mucolytic agent (e.g., N-acetyl-L-cysteine), w/w, acid (e.g., hydrochloric acid) qs to about pH 8.0; and/or a carrier (e.g., an aqueous carrier comprising filtered, purified, distilled, and/or deionized water) qs to 100%. An embodiment can further include about 0.00037%, w/w, visual indicator (e.g., FD&C Blue No. 1).

An embodiment of the present disclosure includes 43.92% chaotropic agent (e.g., guanidine thiocyanate), w/w, ±10%, 2.65% buffering agent (e.g., Tris), w/w, ±10%, 0.81% chelating agent (e.g., EDTA or EDTA disodium (salt) dihydrate), w/w, ±10%, 0.279% surfactant (e.g., SLS), w/w, ±10%, 17.73% alcohol (e.g., SDA 3C or a mixture of 95% ethanol, v/v, ±10%, and 5% isopropanol, v/v, ±10%), w/w, ±10%, 0.093% mucolytic agent (e.g., N-acetyl-L-cysteine), w/w, ±10%, and/or acid (e.g., hydrochloric acid) qs to pH 8.0, ±10%, with a carrier (e.g., an aqueous carrier, preferably filtered, purified, distilled, and/or deionized water) qs to 100%. An embodiment further includes 0.00037%, w/w, ±10% visual indicator (e.g., FD&C Blue No. 1) or equivalent thereof (e.g., 0.185%, w/w, ±10%, of a 0.2%, w/w, ±10% visual indicator concentrate (e.g., in water)). In an embodiment, the amount of each component, ±10%, is further (limited to the recited amount) ±9%, preferably ±8%, more preferably ±7%, still more preferably ±6%, still more preferably ±5%, still more preferably ±4%, still more preferably ±3%, still more preferably ±2%, still more preferably ±1%.

In at least one embodiment, the composition includes about 43.92% guanidine thiocyanate, w/w, about 2.65% Tris, w/w, about 0.81% EDTA or EDTA disodium (salt) dihydrate, w/w, about 0.279% SLS, w/w, about 17.73% SDA 3C, w/w, about 0.093% N-acetyl-L-cysteine, w/w, about 1.08% hydrochloric acid 37%, w/w, or equivalent thereof, or hydrochloric acid qs to a pH of about 8.0, and water qs to 100%, w/w. The composition can include about 0.00037% w/w of FD&C Blue No. 1 (or 0.185% w/w of a 0.2% w/w (in water) concentrate thereof), and about 32.602% water, w/w.

In some embodiments, the composition can be substantially free or devoid of microbial (e.g., bacterial, fungal, and/or viral) contamination. In some embodiments, the composition can have less than or equal to (about) 100 cfu/g bacteria or bacterial contamination. In some embodiments, the composition can have less than or equal to (about) 99, 98, 97, 96, 95, 90, 85, 80, 75, 70, 65, 60, 55, 50, 45, 40, 35, 30, 25, 20, 15, 10, or 5 cfu/g bacteria or bacterial contamination. In some embodiments, the composition can have less than or equal to (about) 100 cfu/g fungus (or fungi, such as yeast and/or mold) or fungal contamination. In some embodiments, the composition can have less than or equal to (about) 99, 98, 97, 96, 95, 90, 85, 80, 75, 70, 65, 60, 55, 50, 45, 40, 35, 30, 25, 20, 15, 10, or 5 cfu/g fungus (or fungi, such as yeast and/or mold) or fungal contamination. As used herein, "cfu/g" refers to colony forming units (of the one or more microbes) per gram (of the (final and/or liquid) composition).

An illustrative embodiment of the present disclosure is presented in Table 1, below. Table 1 describes ingredients of the illustrative composition, as well as the use, function, and/or activity of said ingredients.

TABLE 1

| Ingredients | % w/w |
| --- | --- |
| Purified water—Carrier, base solvent for an aqueous solution | 32.602 |
| Guanidine thiocyanate—Chaotropic agent; solid form. Both guanidinium and thiocyanate ions can be chaotropic; this makes this agent superior to guanidinium chloride (chloride ion is not chaotropic). A chaotropic agent may disrupt (denature) protein structure, aid in releasing protein-bound DNA, lyse cells and virus particles, and denature nucleases, which can damage DNA (and RNA). | 43.92 |
| Tris/Trizma base—Buffering agent; tris(hydroxymethyl)aminomethane; solid form, alternatively 40% (w/w) solution in water. | 2.65 |
| EDTA—Chelating agent; ethyenediaminetetraacetic acid disodium salt dihydrate; solid form. Complexes transition metal ions that are essential for catalyzing DNA (and RNA) degradation by nucleases. In addition, it has antibacterial activity. | 0.81 |
| SLS—Surfactant/detergent; Sodium Lauroyl Sarcosinate; ~30% aqueous stock solution (in water). Alternatively in granulated form. A surfactant may lyse cells, including contaminating microbes (e.g., bacteria), denature proteins, and allow release of nucleic acids. We found that this detergent to be substantially more soluble in our compositions than the more popular sodium dodecyl sulfate (SDS). | 0.93 |
| SDA 3C—Specially Denatured Alcohol (i.e., ethanol, 95%) 3C (isopropanol, 5%). Alcohols may lyse cells, including contaminating microbes (e.g., bacteria) and/or denature proteins. | 17.73 |

TABLE 1-continued

| Ingredients | % w/w |
|---|---|
| FDC Blue No. 1—Visual indicator/coloring agent/dye; ~0.2%, w/w, concentrate (in water). Adds light blue color. It is not essential for DNA stabilization. It aids customer visualization of saliva mixing with stabilizing solution. Predominantly cosmetic. | 0.185 |
| HCl—Hydrochloric acid; ~37% w/w, stock solution (in water); ~12M. Acids may be used to adjust pH of DNA stabilizing solution (e.g., to about 8.0 and/or where the nucleic acid (DNA) is most stable. | 1.08 |
| N-Acetyl-L-cysteine—Mucolytic agent; solid form. Mucolytic agents may aid in denaturing proteins (e.g., by reducing or cleaving disulfide bridges). In addition, ingredients or components (e.g., chemicals or agents) containing free sulfhydryl groups may act as antioxidants and/or may help control dissolved oxygen in the DNA Stabilizing Solution. | 0.093 |
| Batch Total | 100% |

Table 1.1 presents another illustrative formulation for a composition of the present disclosure.

TABLE 1.1

| Ingredients | % w/w |
|---|---|
| Purified water | 34.12 |
| Guanidine thiocyanate | 43.92 |
| Tris/Trizma base | 2.65 |
| EDTA (disodium salt dihydrate) | 0.81 |
| SLS | 0.279 |
| SDA 3C | 17.73 |
| FDC Blue No. 1 | 0.00037 |
| HCl | 0.4 |
| N-Acetyl-L-cysteine | 0.093 |
| Batch Total | 100% |

Additional features of the present disclosure can be learned from U.S. Pat. No. 7,482,116, the entirety of which is incorporate by reference herein.

Kits

Some embodiments include a kit, such as a biological sample preservation kit. In particular, in one or more embodiments, the inventive composition can be incorporated into a kit. Kits can include, for example, a composition, as disclosed and/or described herein, and a sample collection apparatus. In at least one embodiment, the composition can be disposed in a portion of a sample collection apparatus. Illustrative sample collection apparatus can include a container or vial (e.g., a tube) having a sample collection portion. For instance, the container can comprise an outer wall at least partially bounding an internal compartment. The internal compartment can contain the composition, to which a biological sample can be added. Alternatively, the sample can be added to the compartment and the composition added to the sample post-collection. For instance, the apparatus can include a composition dispenser for adding the composition to the compartment, pre- or post-sample collection. In at least one embodiment, the dispenser can comprise a cap for closing or sealing an opening of the apparatus. The opening can lead into or be in fluidic communication with the compartment. The cap can have a compartment for retaining the composition until it is to be added to the compartment of the container.

Some embodiments can include a kit comprising a biological sample collection device (or container) and a composition of the present disclosure. In at least one embodiment, the composition can be disposed in a portion of the device. For instance, in some embodiments, the composition can be disposed in a portion of a cap or lid of the device. The collection device (or container) can be configured to receive the biological sample (e.g., in an inner compartment thereof) and have the composition added thereto.

In some embodiments, the composition in the kit can be substantially free or devoid of microbial contamination (as described above).

Various sample collection apparatus are described in the following applications, the entirety of each of which is incorporated herein by specific reference: U.S. application Ser. No. 14/952,712, filed Nov. 25, 2015; U.S. Provisional Application Ser. No. 62/370,630, filed Aug. 3, 2016; U.S. Provisional Application Ser. No. 62/453,459, filed Feb. 1, 2017; U.S. Provisional Application Ser. No. 62/510,174, filed May 23, 2017; U.S. Provisional Application Ser. No. 62/512,594, filed May 30, 2017; U.S. Provisional Application Ser. No. 62/513,235, filed May 31, 2017; U.S. Provisional Application Ser. No. 62/529,355, filed Jul. 6, 2017; U.S. application Ser. No. 15/667,228, filed Aug. 2, 2017; International Application Serial No. PCT/US2017/045352, filed Aug. 3, 2017; U.S. application Ser. No. 15/692,259, filed Aug. 31, 2017; and U.S. Provisional Application Ser. No. 62/590,165, filed Nov. 22, 2017.

Compositions of the present disclosure can be incorporated into apparatus described in any of the foregoing applications. Embodiments of the present disclosure can include a kit comprising a composition, as disclosed and/or described herein, and a sample collection apparatus described in any of the foregoing applications.

Methods of Manufacture

Some embodiments include a method of manufacturing a composition of the present disclosure. Embodiments can include providing or obtaining a carrier, as described herein. Embodiments can include adding to the carrier a suitable amount of one or more components or ingredients described herein (e.g., to a final concentration described herein). Embodiments can include adding to the carrier a described amount of stock solution of one or more components or ingredients described herein.

At least one embodiment includes adding to the carrier a chaotropic agent, buffering agent, chelating agent, surfactant, alcohol, acid, and/or mucolytic agent. One or more embodiments can include adding to the carrier a visual indicator. At least one embodiment includes adding to a (liquid) carrier, chaotropic agent to a final concentration of 20-50%, w/w, buffering agent to a final concentration of 0.1-5%, w/w, chelating agent to a final concentration of 0.01-5%, w/w, surfactant to a final concentration of 0.01-5%, w/w, alcohol to a final concentration of 5-25%, w/w, acid to pH 6.5-9.5 or equivalent amount, and/or mucolytic agent to a final concentration of 0.005-0.25%, w/w. At least one embodiment includes adding to a (liquid) carrier visual indicator to a final concentration of 0.00005-0.5%, w/w. The carrier can be included at qs to 100%

At least one embodiment includes adding to a (liquid) carrier, chaotropic agent to a final concentration of (about) 43.92%, w/w, buffering agent to a final concentration of (about) 2.65%, w/w, chelating agent to a final concentration of (about) 0.81%, w/w, surfactant to a final concentration of (about) 0.279%, w/w, alcohol to a final concentration of (about) 17.73%, w/w, acid to pH (about) 6.5-9.5 or to a final concentration of (about) 0.4%, w/w, and/or mucolytic agent to a final concentration of (about) 0.093%, w/w. At least one embodiment includes adding to a (liquid) carrier visual indicator to a final concentration of (about) 0.00037%, w/w. The carrier can be included at (about) 34.12% or qs to 100%.

In some embodiments, the chaotropic agent can be or comprise guanidine and/or thiocyanate, the buffering agent can be or comprise Tris or Trizma base, the chelating agent can be or comprise EDTA or EDTA disodium (salt) dihydrate, the surfactant can be or comprise SLS, the alcohol can be or comprise ethanol and/or isopropanol (e.g., SDA 3C), the mucolytic agent can be or comprise N-acetyl-L-cysteine, the acid can be or comprise HCl, the carrier can be or comprise water, and/or the optional visual indicator can be or comprise FD&C Blue No. 1.

A method of manufacturing a nucleic acid stabilization and/or preservation composition can include adding the carrier to a vessel (e.g., charging a mixing tank with (filtered, deionized, etc.) water. In some embodiments, the carrier can be included at a final concentration of about 34.12%, w/w, of the composition or to qs 100%.

In some embodiments, a mixer can be activated before one or more additional components or ingredients are added to the carrier. In some embodiments, a mixer can be activated after one or more additional components or ingredients are added to the carrier. In some embodiments, a mixer can be set to a speed setting of 2-8, preferably 3-7, more preferably 4-6, still more preferably 5 and/or sweep setting of 2-8, preferably 3-7, more preferably 4-6, still more preferably 5. In some embodiments, the carrier can be heated to a suitable mixing temperature before one or more additional components or ingredients are added to the carrier. In some embodiments, the carrier can be heated to a suitable mixing temperature after one or more additional components or ingredients are added to the carrier. In some embodiments, the suitable mixing temperature can be (about) 55-95±5° F., preferably 60-90±5° F., more preferably 65-85±5° F., still more preferably 70-80±5° F., most preferably 75±5° F.

In some embodiments, a suitable amount of chaotropic agent (e.g., guanidine thiocyanate) can be added to the carrier (e.g., to a final concentration of about 43.92%, w/w of the composition). In some embodiments, the chaotropic agent can be mixed for a period of time (e.g., between 30-300 minutes, preferably 60-240 minutes, more preferably 120-180, still more preferably 140-160 minute, most preferably 150 minutes, or until the chaotropic agent is dissolved (in solution) in the carrier.

In some embodiments, a suitable amount of buffering agent (e.g., Tris or Trizma Base) can be added to the carrier (e.g., to a final concentration of about 2.65%, w/w of the composition). In some embodiments, the buffering agent can be mixed in for a period of time (e.g., between 1-90 minutes, preferably 5-60 minutes, more preferably 10-45, still more preferably 12-30 minute, still more preferably 15-25 minute, most preferably (about) 20 minutes, or until the buffering agent is dissolved (in solution) in the carrier.

In some embodiments, a suitable amount of chelating agent (e.g., EDTA, EDTA disodium salt, EDTA disodium (salt) dihydrate) can be added to the carrier (e.g., to a final concentration of about 0.81%, w/w of the composition). In some embodiments, the chelating agent can be mixed in for a period of time (e.g., between 1-90 minutes, preferably 5-60 minutes, more preferably 10-45, still more preferably 12-30 minute, still more preferably 15-25 minute, most preferably (about) 20 minutes, or until the chelating agent is dissolved (in solution) in the carrier. In at least one embodiment, the buffering agent and the chelating agent can be added to the carrier together, at (approximately) the same time, contemporarily, concomitantly, and/or (substantially) concurrently (or simultaneously), with or without being pre-mixed together. In some embodiments, the buffering agent and the chelating agent can be added to the carrier separately.

In some embodiments, a suitable amount of surfactant (e.g., SLS) can be added to the carrier (e.g., to a final concentration of about 0.279%, w/w of the composition). In some embodiments, the surfactant can be mixed in for a period of time (e.g., between 1-90 minutes, preferably 5-60 minutes, more preferably 10-45, still more preferably 15-35 minute, still more preferably 20-30 minute, most preferably (about) 25 minutes, or until the surfactant is dissolved (in solution) in the carrier.

In some embodiments, a suitable amount of alcohol (e.g., ethanol, a mixture of ethanol and another chemical, such as isopropanol, or a SDA, preferably SDA 3C) can be added to the carrier (e.g., to a final concentration of about 17.73%, w/w of the composition). In some embodiments, the alcohol can be mixed in for a period of time (e.g., between 5-90 minutes, preferably 10-75 minutes, more preferably 15-60, still more preferably 25-45 minute, still more preferably 30-40 minute, most preferably (about) 35 minutes, or until the alcohol is dissolved (in solution) in the carrier.

In some embodiments, a suitable amount of an optional visual indicator (e.g., a coloring agent, a dye, preferably a blue dye, such as FD&C Blue No. 1) can be added to the carrier (e.g., to a final concentration of about 0.00037%, w/w of the composition). In some embodiments, the visual indicator can be mixed in for a period of time (e.g., between 5-90 minutes, preferably 10-60 minutes, more preferably 15-45, still more preferably 10-30 minute, still more preferably 15-25 minute, most preferably (about) 20 minutes, or until the alcohol is dissolved (in solution) in the carrier.

In some embodiments, a suitable amount of an acid (e.g., hydrochloric acid) can be added to the carrier (e.g., to a final concentration of about 0.4%, w/w of the composition or to a pH 8.0 of the composition). In some embodiments, the acid can be mixed in for a period of time (e.g., between 5-90 minutes, preferably 10-60 minutes, more preferably 15-45, still more preferably 10-30 minute, still more preferably 15-25 minute, most preferably (about) 20 minutes, or until the acid is dissolved (in solution) in the carrier and/or the mixture equilibrates at the desired pH.

In some embodiments, a suitable amount of a mucolytic agent (or reducing agent) (e.g., N-Acetylcysteine, N-acetyl-L-cysteine) can be added to the carrier (e.g., to a final concentration of about 0.093%, w/w of the composition). In some embodiments, the acid can be mixed in for a period of time (e.g., between 5-90 minutes, preferably 10-60 minutes, more preferably 15-45, still more preferably 10-30 minute, still more preferably 15-25 minute, most preferably (about) 20 minutes, or until the acid is dissolved (in solution) in the carrier and/or the mixture equilibrates at the desired pH.

A series of illustrative manufacturing batch procedures are present in Table 3.

TABLE 3

| Process Parameter | Batch #1 | Batch #2 | Batch #3 | Batch #4 |
|---|---|---|---|---|
| 3.1 Addition of Water | | | | |
| Mixing Speed (mixer/sweep) | 5/5 | 4/4 | 6/6 | 5/5 |
| 3.2 Addition of Guanidine Thiocyanate | | | | |
| Mixing Speed (mixer/sweep) | 5/5 | 4/4 | 6/6 | 5/5 |
| Mixing Time | 150 min | 120 min | 180 min | 150 min |
| 3.3 Addition of Trizma Base and Disodium EDTA | | | | |
| Addition Temperature | 70° F. | 65° F. | 75° F. | 70° F. |
| Mixing Speed (mixer/sweep) | 5/5 | 4/4 | 6/6 | 5/5 |
| Mixing Time | ≥75 min | ≥60 min | ≥90 min | ≥75 min |
| 3.4 Addition of Sodium Lauroyl Sarcosinate and SDA 3C | | | | |
| Mixing Speed (mixer/sweep) | 5/5 | 4/4 | 6/6 | 5/5 |
| Mixing Temperature | 75 ± 5° F. | 70° F. | 80° F. | 75 ± 5° F. |
| Mixing Time | 25 min | 20 min | 30 min | 25 min |
| 3.5 Addition of Hydrochloric Acid | | | | |
| Mixing Speed (mixer/sweep) | 5/5 | 4/4 | 6/6 | 5/5 |
| Mixing Temperature | 75 ± 5° F. | 70° F. | 80° F. | 75 ± 5° F. |
| Mixing Time | 20 min | 15 min | 25 min | 20 min |
| 3.6 Addition of Color Concentrate | | | | |
| Mixing Speed (mixer/sweep) | 5/5 | 4/4 | 6/6 | 5/5 |
| Mixing Temperature | 75 ± 5° F. | 70° F. | 80° F. | 75 ± 5° F. |
| Mixing Time | 20 min | 15 min | 25 min | 20 min |
| 3.7 Addition of N-Acetylcysteine | | | | |
| Mixing Speed (mixer/sweep) | 5/5 | 4/4 | 6/6 | 5/5 |
| Mixing Temperature | 75 ± 5° F. | 70° F. | 80° F. | 75 ± 5° F. |
| Mixing Time | 45 min | 30 min | 60 min | 45 min |

Quality control testing can be performed at any suitable point during manufacture. For example, upon completion of the bulk manufacturing process for each batch, two (2) samples (approximately 4 ounces each) were aseptically obtained from the bulk blend tank using clean and sanitized, approved and appropriate tools for obtaining samples from each of the following locations: top surface of batch near center of tank, top surface of batch near side wall of tank, middle of batch near center of tank, middle of batch near side wall of tank, bottom of batch near center of tank, and bottom of batch near side wall of tank. Each sample was placed in a sterile cup and labeled.

Each sample was tested for proper appearance, specific gravity, and pH. In addition, assays were performed to test concertation and/or effectiveness of the chelating agent, alcohol, and mucolytic agent. In addition, contamination (microbial limits) were tested by measuring total aerobic plate count, yeast and mold, *Staphylococus aureus*, and *Pseudomonas aeruginosa*. Table 4 presents testing specifications for various quality control measures.

TABLE 4

| TEST | METHOD | SPECIFICATION |
|---|---|---|
| Appearance | SOP 403 | Comparable to Standard |
| Specific gravity @ 25° C. | SOP 405 | Report only |
| pH | STM M403 | 7.9-8.3 |
| Assay - Disodium EDTA | Cornerstone | 0.73-0.89% |
| Assay - SDA Alcohol 3C | Cornerstone | 15.96-19.50% |
| Assay - N-Acetylcysteine | Cornerstone | 0.084-0.102% |
| Microbial limits | STM M429 | Less than 100 cfu/g |
| Yeast and mold | STM M429 | Less than 100 cfu/g |

TABLE 4-continued

| TEST | METHOD | SPECIFICATION |
|---|---|---|
| *Staphylococcus aureus* | STM M429 | Absence |
| *Pseudomonas aeruginosa* | STM M429 | Absence |

In some embodiments, the method can include sealing the composition in a suitable storage vessel or a portion of a sample collection apparatus (e.g., a composition storage portion of a container or vial (e.g., a tube). Samples were also subjected to controlled room temperature (CRT) and accelerated (ACC) stability testing in storage vessels and sample collection apparatus.

In some embodiments, the method can produce or result in a composition that can be substantially free or devoid of microbial contamination (as described above).

Methods of Use

Some embodiments include a method of preserving and/or stabilizing nucleic acid. The method can comprise providing a biological sample containing the nucleic acid and combining a composition of the present disclosure with the biological sample. In at least one embodiment, the biological sample can be a mucin-containing bodily fluid or tissue, such as sputum or saliva. The method can include reducing the viscosity of a mucin-containing bodily fluid or tissue (e.g., by reducing disulfide bonds inherent to mucin with a mucolytic agent or reducing agent).

In at least one embodiment, the nucleic acid is DNA. In some embodiments, the composition can stabilize the nucleic acid or DNA (e.g., against degradation). In some embodiments, the composition can stabilize the nucleic acid or DNA for a first period of time. In some embodiments, the first period of time can be greater than or equal to about 14 days, 30 days, 60 days, 90 days, 120 days, 240 days, 300 days, or 365 days. In some embodiments, the composition can stabilize the nucleic acid or DNA for the first period of time at room temperature, between −20° C. to 50° C., or other suitable temperature or temperature range. In some embodiments, the composition can be stable for a second period of time. In some embodiments, the second period of time can be greater than or equal to about 12 months, 18 months, 24 months, 30 months, or 36 months. In some embodiments, the composition can be stabile for the second period of time at room temperature, between −20° C. to 50° C., or other suitable temperature or temperature range.

At least one embodiment includes a method of recovering a nucleic acid from sputum, comprising: i) obtaining sputum from a subject, ii) contacting the sputum with a composition of the present disclosure to form a sample mixture, iii) optionally contacting the mixture with a protease, and iv) recovering the nucleic acid from the mixture.

In some embodiments, the composition does not significantly inhibit or interfere with subsequent nucleic acid analysis, such as DNA amplification (via PCR), (next generation) sequencing, and so forth, when added in a suitable amount to the biological sample.

Sample Collection

Some embodiments of the present disclosure include obtaining, providing, and/or collecting a biological sample (e.g., from a subject, such as a human subject). In some embodiments, the biological sample can be or comprise (human) saliva. The (human) sample can be collected aseptically (to avoid (microbial) contamination). In one or more embodiments, the sample can be collected into a sample collection apparatus or sample container thereof. In some embodiments, the sample collection apparatus or container can be part of a kit and/or can include a composition of the present disclosure. Embodiments can include contacting the sample with a composition of the present disclosure.

DNA Extraction and Analysis:

Some embodiments of the present disclosure include extracting nucleic acid from the biological sample. The following is a non-exhaustive listing or description of various modes of extraction or extraction procedures that may be suitable for use with compositions of the present disclosure.

Extraction Chemistry

Organic—Phenol chloroform extraction is still a mechanism employed in both research and clinical labs and is sample type dependent when it comes to tissue source. A manual phenol/chloroform extraction followed by a chloroform back extraction to help remove any organic solvent contamination will be performed to extract high molecular weight genomic DNA.

Salting out—Both home brew and commercial salting out chemistries are widely used for high molecular weight nucleic acid extraction. The approach requires a high concentration of salt be added to the saliva sample in order to crash out nucleic acid under the addition of ethanol. A series of washes are performed to remove excess salt from the sample prior to analysis.

Solid phase—A variety of technology providers offer both spin column and vacuum manifold solutions for binding DNA to a solid support for nucleic acid purification. Once the DNA is attached to the support a series of washes are performed. Ultimately DNA is eluted off of the solid support in a small volume for analysis. Spin column chemistry is frequently used in both the research and clinical lab.

Bead-based—Beads or (para)magnetic beads are prepared with various binding moieties or by charge in order to bind high molecular weight DNA. The beads are captured by a magnetic field so anything unbound to the beads can be washed away as part of the purification process. Once washing is complete the nucleic acid is eluted off of the beads with a solution that solubilizes the DNA leaving the beads behind which are subsequently removed by reapplying a magnetic field. There are both small and large volume automated solutions for this approach in the research and clinical environment.

Illustrative Extractions

Ten DNA samples previously extracted from the saliva collection kits containing compositions of the present disclosure and up to six samples from an existing saliva collection kit were used for testing. An additional 23 samples were newly collected using the inventive saliva collection kit. Each of the 23 samples were extracted in duplicate 700 ul aliquots. Standard QC was performed to assess the quality of the DNA.

23/23 samples were extracted with two replicates per sample. Average combined yield by UV spectrophotometry (Nanodrop) of all samples was 20.4ug (2.8-111.4). 20/23 extractions had 260/280 ratios above the desired value of 1.7, although the three samples lower than 1.7 are likely to perform well in downstream analysis. All samples had high molecular weight DNA, as shown in FIG. 1A.

700 ul of saliva sample solution was extracted using Perkin Elmer reagents for the MSM1 (Chemagen) extraction system. Concentrations for all of the samples were determined by UV spectrophotometry (Nanodrop). An estimate of purity was determined with UV spectrophotometry by measuring the A260/A280 absorbance ratio. Additionally, samples were analyzed on an agarose gel to visualize sample integrity. A molecular weight sizing ladder (L) and a control sample of greater than 50 kb (C) are included on each gel. Bionexus All Purpose HI-LO DNA Marker Used on Qualitative Gels (see FIG. 3B).

Analytical Approaches

Some embodiments include analyzing the extracted nucleic acids. Several methods are available for analyzing the extracted nucleic acids. The following is a non-exhaustive listing or description of various methods for analyzing the extracted nucleic acids that may be suitable for use with compositions of the present disclosure.

PCR

Polymerase Chain Reaction (PCR) analysis is a rapid and cost effective means for assessing the fidelity and cleanliness of DNA templates. A series of PCR reactions (of varying size amplicons) will be generated from all DNA templates and resolved via electrophoresis for the correct size amplification product. The range of PCR amplicon sizes will provide information on the fidelity of all DNA extraction products.

qPCR

Quantitative PCR (qPCR) uses dual labeled fluorogenic probes for the quantitation of PCR amplicons. Allelic discrimination utilizing Taqman chemistry will be used to determine the specific genotype for all DNAs collected and extracted across all extraction approaches. Genotypes for each of the subjects will be measured for concordance across all variables being analyzed. All quantitative measurements will be made in triplicate.

dPCR

Digital PCR (dPCR) is an emerging technology being employed for sensitive detection of genotypes in samples with limiting amounts and/or limiting quality. The same Taqman assays will be used to determine the absolute sensitivity of every DNA sample extracted. Given the sensitivity of dPCR we will be able to determine the ultimate sensitivity of each variant being analyzed.

Microarray

The measurement of hundreds of thousands or millions of SNPs simultaneously has tremendous implications when it comes to both discovery and clinical classification of a single DNA sample. The sensitivity and specificity requirements are quite different than QPCR based analysis and the approach for SNP detection is also different as this analytical approach uses a hybridization based mechanism for identifying DNA variants. Call rates and SNP concordance across donors processed with different DNA extraction chemistries will be a critical analytical endpoint.

Sanger Sequencing

The gold standard for variant analysis will be employed across all samples in this study. The target regions for analysis will cover the same amplicons of QPCR, dPCR and Microarray to cross validate the genotypes across all other analytical methods. The ability to make high quality sanger base calls (and hence variants) is highly dependent on the quality of nucleic acid. This approach is used regularly for clinical analysis.

NextGen Sequencing

As used herein, "next generation sequencing" (NGS), also known as high-throughput sequencing, refers to non-Sanger-based, high-throughput DNA sequencing technologies. Through NGS, millions or even billions of DNA strands can be sequenced in parallel, yielding substantially more throughput and minimizing the need for the fragment-cloning methods that are often used in Sanger sequencing of genomes. NGS is the catch-all term used to describe a number of different modern sequencing technologies or platforms including, for example, pyrosequencing, sequencing by synthesis, sequencing by ligation, ion semiconductor sequencing, and others as known in the art.

As understood by those skilled in the art, NGS generally allow sequencing of large amounts of DNA and RNA much more quickly and affordably than Sanger sequencing. In NGS, vast numbers of short reads are sequenced in a single stroke. To do this, firstly the input sample can be cleaved into short sections. The length of these sections depends on the particular sequencing machinery used. Illustrative examples of specific NGS technologies include, for example, Illumina® (Solexa) sequencing, Roche 454™ sequencing, Ion torrent™: Proton/PGM sequencing, SOLiD sequencing, and so forth.

In Illumina sequencing, 100-150 bp reads are used. Somewhat longer fragments are ligated to generic adaptors and annealed to a slide using the adaptors. PCR is carried out to amplify each read, creating a spot with many copies of the same read. They are then separated into single strands to be sequenced. The slide is flooded with nucleotides and DNA polymerase. These nucleotides are fluorescently labelled, with the color corresponding to the base. They also have a terminator, so that only one base is added at a time. An image is taken of the slide. In each read location, there will be a fluorescent signal indicating the base that has been added. The slide is then prepared for the next cycle. The terminators are removed, allowing the next base to be added, and the fluorescent signal is removed, preventing the signal from contaminating the next image. The process is repeated, adding one nucleotide at a time and imaging in between. Computers are then used to detect the base at each site in each image and these are used to construct a sequence. All of the sequence reads will be the same length, as the read length depends on the number of cycles carried out.

Roche 454™ sequencing can generally sequence much longer reads than Illumina®. Like Illumina®, it does this by sequencing multiple reads at once by reading optical signals as bases are added. As in Illumina®, the DNA or RNA is fragmented into shorter reads, in this case up to 1 kb. Generic adaptors are added to the ends and these are annealed to beads, one DNA fragment per bead. The fragments are then amplified by PCR using adaptor-specific primers. Each bead is then placed in a single well of a slide. So each well will contain a single bead, covered in many PCR copies of a single sequence. The wells also contain DNA polymerase and sequencing buffers. The slide is flooded with one of the four NTP species. Where this nucleotide is next in the sequence, it is added to the sequence read. If that single base repeats, then more will be added. So if we flood with Guanine bases, and the next in a sequence is G, one G will be added, however if the next part of the sequence is GGGG, then four Gs will be added. The addition of each nucleotide releases a light signal. These locations of signals are detected and used to determine which beads the nucleotides are added to. This NTP mix is washed away. The next NTP mix is now added and the process repeated, cycling through the four NTPs. This kind of sequencing generates graphs for each sequence read, showing the signal density for each nucleotide wash. The sequence can then be determined computationally from the signal density in each wash. All of the sequence reads we get from 454 will be different lengths, because different numbers of bases will be added with each cycle.

Unlike Illumina® and Roche 454™, Ion torrent™ and Ion proton sequencing do not make use of optical signals. Instead, they exploit the fact that addition of a dNTP to a DNA polymer releases an H+ ion. As in other kinds of NGS, the input DNA or RNA is fragmented, this time ~200bp. Adaptors are added and one molecule is placed onto a bead. The molecules are amplified on the bead by emulsion PCR. Each bead is placed into a single well of a slide Like Roche 454™, the slide is flooded with a single species of dNTP, along with buffers and polymerase, one NTP at a time. The pH is detected is each of the wells, as each H+ ion released will decrease the pH. The changes in pH allow us to determine if that base, and how many thereof, was added to the sequence read. The dNTPs are washed away, and the process is repeated cycling through the different dNTP species. The pH change, if any, is used to determine how many bases (if any) were added with each cycle.

Additionally, or alternatively, the sequencing may be more generally performed by a fluorescent-based sequencing technique and/or any electrical-current-based sequencing technique. Illustrative examples of fluorescent-based sequencing techniques include any technique that incorporates nucleotides conjugated to a fluorophore, such as, for example sequencing using Illumina® based sequencing methods and systems. Illustrative examples of electrical-current-based sequencing techniques include any sequencing technique (including strand sequencing methods) that measures the electrical current of a polynucleotide as it passes through a pore inserted into a charged membrane or otherwise specifically disrupts the electrical current of a sensor and/or charged membrane. A non-limiting example of electrical-current-based sequencing techniques include the Nanopore DNA sequencing systems and methods of Oxford NanoPore Technologies®.

Strand sequencing systems, such as those provided by Oxford NanoPore Technologies®, provide some advantages when determining copy number variation of a nucleic acid, particularly the copy number variation of a sample that potentially contains DNA (or other nucleic acid) from neoplastic and/or cancerous cells. For example, in strand sequencing techniques, a single portion of the genome is continuously sequenced, which allows a direct analysis of copy number variation instead of an implicit analysis of copy number variation that may occur when analyzing sequencing data provided by other sequencing methods where the sample nucleic acid is cut into small fragments for sequencing. This may be particularly advantageous for embodiments when sequence coverage is low. That is, in some embodiments, a low sequence coverage run may return an incomplete set of genomic data. It may be possible to infer from the sequence data the presence and/or absence of genomic regions in addition to an implicit copy number for each sequenced region. However, in a strand sequencing method, the long sequence reads produced may allow for a more definitive assessment of copy number variation, particularly for regions that are duplicated or deleted. If a full sequence is not available due to the low coverage of the sequencing run, it may be difficult to determine what portions of the genome are deleted (a form of copy number variation) versus what portions of the genome were not represented based on statistical probability (i.e., random sampling).

As an illustrative example, a sequencing run that generates data having 0.5× coverage will theoretically leave half of the sample unrepresented. Using sequencing methods that "chop up" the nucleic acid into small fragments for sequencing, the final product may be a sequence library representing about half of the total reference genome, where an aligned reference genome is littered with a smattering of smaller nucleic acid matches. On the other hand, using a strand sequencing method, again at low coverage (e.g., 0.5×), the result may be a sequence library representing, again, about half of the total reference genome. However, when aligned with a reference genome, the matching portions are much longer and may provide more definitive information, such as what sequences have been deleted, duplicated, inserted, etc. This may also prove problematic. While a longer contiguous portion of the genome may be represented by a strand sequencing approach, long contiguous portions of the genome are also left unknown. So, although strand sequencing methods may allow for a higher definition view of portions of the genome, smaller sequencing reads have the potential to provide a more global picture of the entire genome. In in this and other ways, strand sequencing may provide a robust model for analyzing copy number variation.

Though the foregoing is illustrative of known sequencing techniques and their applications to the inventive methods and systems disclosed herein, it should be understood that this does not preclude as yet undiscovered or otherwise undisclosed sequencing methods from being applied within the scope of the present invention. That is, the sequencing method, itself, is not, in many embodiments, a requisite inventive step (unless, for example, an improvement is provided to the method and/or system through use of a particular sequencing technique); rather, what is done with the sequencing data provided by the sequencing method and/or how those data are applied generally comprises an inventive step. Accordingly, it should be appreciated that future sequencing technologies (and those sequencing technologies that have not been explicitly listed herein), if used as a tool in the disclosed method or systems, are included within the scope of this application.

Additionally, any of the foregoing sequencing techniques may be used in any number or capacity and with any number of flow cells or other similar inputs that affect the total number of sequencing reads provided for each sequencing reaction/run.

Next Generation sequencing may ultimately become the standard for analysis of both DNA and RNA targets. A targeted panel including the genomic regions covered by qPCR, dPCR and array based targets is created for all DNA samples through a standard library preparation process. Samples are barcoded and multiplexed on a NextGen platform for variant analysis. Data is de-multiplexed and analyzed for direct comparison of genotype call across all other platforms.

Several of the above and other DNA-based downstream methods were tested to assess the quality and usability of DNA extracted from samples collected using 2 mL saliva collection kits containing a nucleic acid preservative composition of the present disclosure. Additionally, a small number of DNA samples, extracted from two existing products were used for comparison for some downstream methods. Below is a non-exhaustive listing or description of several downstream methods tested, including TaqMan® chemistry for detection of single nucleotide polymorphisms (SNPs) using an OpenArray® format (n=120 SNPs/sample), a copy-number variant (CNV) using TaqMan® chemistry (CYP2D6 gene), whole exome next-generation sequencing (WES) (Thermo Fisher) and chromosomal microarray analysis (CMA) (Affymetrix CytoScan HD). These methods were chosen to include a wide variety of common methods used in molecular genetics laboratories. In addition to the downstream analysis, the bacterial DNA content as a percentage of total DNA was measured using a quantitative PCR (qPCR) assay. Without being bound to any theory, saliva samples are known have high concentration of bacterial DNA that could be an interfering substance for some methods.

TaqMan® Open Array® SNP Genotyping

Genotyping for the single nucleotide polymorphism was accomplished using a TaqMan® OpenArray® genotyping assay. The TaqMan® assay is an allele discrimination assay using PCR amplification and a pair of fluorescent dye detectors that target the SNP. One fluorescent dye is attached to the detector that is a perfect match to the first allele (e.g. an "A" nucleotide) and a different fluorescent dye is attached to the detector that is a perfect match to the second allele (e.g. a "C" nucleotide). During PCR, the polymerase will release the fluorescent probe into solution where it is detected using endpoint analysis in a Life Technologies, Inc. Specifically OpenArray® technology is a nanoliter fluidics platform for low-volume solution-phase reactions. The OpenArray® technology uses a microscope slide-sized plate with 3,072 through holes. Each through-hole is 300 μm in diameter and 300 μm deep and is treated with hydrophilic and hydrophobic coating. TaqMan® chemistry for a single assay is preloaded and dried down in each through hole. OpenArrays® were obtained through Life Technologies design and manufacturing. Genotypes were determined using Life Technologies' Taqman Genotyper v1.0.1 software.

A total of 5234 genotypes were determined on 44 samples on a 118-120 SNPs/sample. The 44 samples included repeats of 3 samples each from extractions from both the inventive and existing kits. Genotyping of samples from the inventive kits was highly successful and exceeded know performance expectations for this type of assay. Without being bound to any theory, Taqman genotyping is expected to successfully yield genotyping on greater than 99% of samples. In this experiment, 99.75% of samples produced a genotype (5221/

5234). There were no significant differences in genotyping rate between the inventive solution DNA extracts and the existing extracts, 99.74% and 99.87%, respectively. In the 6 samples duplicated in both the inventive solution DNA extracts and the existing extracts, all genotypes were concordant.

Taqman® Copy-Number Variant Detection

A TaqMan® Copy Number Assay (CYP2D6-Hs00010001_cn) was used to detect the copy number of the CYP2D6 gene, a well characterized CNV evaluated in pharmacogenetics. TaqMan® Copy Number Assays employ TaqMan® MGB probe chemistry to evaluate the copy number of genomic DNA targets. This assay used an Applied Biosystems® 7900 HT real-time PCR instruments and copy caller software to determine the copy number. Each sample was amplified three times and plotted against a standard curve to determine copy number.

33 inventive extracted DNA samples and 5 existing extracted samples were analyzed for a well-characterized copy number variant in the CYP2D6 gene. 30/33 inventive solution extracted DNA samples produced CNV results. 5/5 competitor extracted samples produced CNV results. The 3 samples that did not produce a CNV result were all from the same person ("B") from 3 independent samples collected on the same day. A sample from this same individual that was collected on a different day and extracted from the existing saliva kit did produce a normal CNV result ruling out a potential interfering mutation.

Whole Exome Sequencing (WES)

An exome library was prepared using Ion AmpliSeq™ Exome Kit. The library kit is combined with Ampliseq Exome Panel Primer pools, which contains approximately 294,000 primers pairs across 12 primer pools. The targeted resulting amplicons are then treated with a reagent to partially digest the primers and phosphorlyate the amplicons. The amplicons are then ligated to Ion Adapters with barcodes and purified. Upon the completion of the exome library preparation, the purified, exome-enriched library is quantified by real-time PCR. The quantified library is then diluted to 100 pM and used to prepare templated Ion PI™ Ion Sphere™ Particles (ISPs) for sequencing. The sample was then sequenced on the Ion Proton System using an Ion PI™ Chip v3. Ion Hi-Q Sequencing 200 V2 chemistry was used to sequence up to 200-base pair average insert libraries.

Four samples, 3 extracted from the inventive saliva kit and one extracted from the existing saliva kit were evaluated with a whole exome library prep (AmpliSeq Exome, Thermo Fisher) followed by next generation sequencing on the Ion Proton instrument (Thermo Fisher). Typically expected results are >30 million reads, mean depth of coverage of greater than 80× and >80% of bases covered at a depth of >20×. Three of four samples met these criteria. There was one inventive saliva kit extracted sample that did not meet two of the three QC metrics having <30 million reads and less that 80× mean depth coverage. It is noted that the underperforming sample was one of the same samples that also did not have a successful CNV analysis. Examination of the DNA QC profile did point to anything unusual about this sample. All QC metrics were met. Although underperforming this sample yielded adequate exome sequencing results for evaluation.

Chromosomal microarray (CMA)

The CMA analysis was conducted using the Affymetrix CytoScan HD assay following the manufacturer's protocol. The samples were scanned on a Genome Analyzer 3000. Chromosomal microarrays were used to detect chromosomal aberrations at a higher resolution than karyotyping. The assay consisted of DNA preparation followed by hybridization to the CytoScan HD chip that contains approximately 2.7 million CNVs across the genome. The samples were evaluated using the Affymetrix ChAS software.

One sample was selected from the Spectrum saliva kit extracted DNAs. It was successfully evaluated on a chromosomal microarray (Affymetrix, CytoScan HD). The sample had a MAPD value of ≤0.25 (0.18), SNPQC value of ≥15 (16.47), a waviness value of ≤0.12 (0.09) and a QC call rate of ≥95% (96.8%).

Bacterial DNA Content Using a qPCR Assay

Bacterial DNA content with in the sample was determined using a modified protocol described in the literature. Briefly, a standard curve was created using a serial dilution of *E. coli* to compare to real time PCR data generated. PCR primers were chosen from a region of the 16S rRNA gene that is known to be conserved across a wide variety of microorganisms and is not found in eukaryote DNA. The DNA was tested for the presence of the 16S rRNA gene using real-time qPCR on a ThermoFisher 7900HT instrument using copy caller software.

Bacterial DNA content, as a percentage of the total amount of DNA from the saliva collected sample, has been thought to possibly inhibit or reduce the success rate of the downstream analysis. 33 DNA samples extracted from the inventive saliva kit and 5 DNA samples extracted from the existing saliva kit were tested for the percentage of bacterial DNA present. Previous data from the competitor estimated the percentage of bacterial DNA to be approximately 13%. The average bacterial content of the inventive saliva kit extractions was 5.5% (1.1-14.3%). The average bacterial content of the competitor saliva kit extractions was 26% (2.1-96.2%)-14.31%).

A series of the above and/or other experimental tests were performed to support an FDA submission for 510K consideration in order to obtain approval for use of a formulation of the present disclosure in a collection device for nucleic acid extraction using any one of a variety of available chemistry approaches, including organic, solid-phase, bead-based, and salting out extraction, as well as any one of a variety of currently used molecular analysis, including PCR, qPCR, dPCR, microarray, Sanger sequencing, and so-called next generation (or NextGen) sequencing (NGS), as outlined in Table 5, below.

TABLE 5

| Extraction Chemistry/ Analytical Platform | PCR | QPCR | dPCR | Microarray | Sanger Sequencing | NextGen Sequencing |
|---|---|---|---|---|---|---|
| Organic | X | X | X | X | X | X |
| Solid-phase | X | X | X | X | X | X |
| Bead-based | X | X | X | X | X | X |
| Salting out | X | X | X | X | X | X |

Summary of Results

DNA was successfully extracted from all samples in all replicates. In general, the size (and yield) of the extracted DNA was high. There was minimal evidence of degradation. The replicates from a sample were very comparable in terms of yield. Additionally, the yields across what are assumed to be the same individual behaved similarly. Genotyping for SNPs produced a high quality result and met expected yield. Samples from one individual, 4 separately collected samples, did not meet QC metrics for the CNV (n=3) or NGS (n=1). Bacterial DNA content as a percentage of the total DNA was relatively low in the inventive saliva kit DNA extractions.

In a further example, presented in Tables 6 and 7, 100 samples were used to test the performance of a nucleic acid preservative composition of the present disclosure ("Inventive") and two existing products ("Existing 1" and "Existing 2"). As presented in Table 6, the "Inventive" nucleic acid preservative composition of the present disclosure yielded a higher average concentration of DNA and a higher amount (yield) of total DNA than either of the "Existing" products.

TABLE 6

| Kit | Average Conc. (ng/ul) | Average Volume (ul) | Average Yield (ug) |
|---|---|---|---|
| Existing 1 | 124.50 | 460.44 | 47.32 |
| Inventive | 152.26 | 436.23 | 62.05 |
| Existing 2 | 145.42 | 438.59 | 58.16 |

As further presented in Table 7, samples processed with the "Inventive" nucleic acid preservative composition of the present disclosure had a significantly lower average amount of non-human DNA than either of the "Existing" products.

TABLE 7

| Kit | Average 260/230 | Average 260/280 | Average FQC % | Average Non-Human DNA % | Overall Viscosity Score |
|---|---|---|---|---|---|
| Existing 1 | 1.30 | 1.72 | 96.7 | 9.3 | 5 |
| Inventive | 0.83 | 1.79 | 98.9 | 4.5 | 3 |
| Existing 2 | 1.08 | 1.71 | 95.6 | 11.2 | 6 |

Accordingly, compositions of the present disclosure are surprisingly, significantly superior to existing DNA preservation products. In particular, it was surprising and unexpected that the compositions of the present disclosure work so well (e.g., yield high amounts of (human) nucleic acid (DNA) and/or have or exhibit low levels of microbial contamination). It was further surprising and unexpected that the compositions of the present disclosure work so well with the low amount of alcohol provided in some embodiments. For instance, in some embodiments, the amount of alcohol included in the composition can be less (e.g., about 20%, 25%, 30%, 35%, 40%, 45%, 50%, 55%, or 60% less) than typical, traditional, or existing nucleic acid preservation solutions. In addition, the lower amount of alcohol of more economical and/or makes the composition more amendable to shipping or transport (e.g., by more easily complying with shipping requirements and regulations, reducing volatility, etc.).

Conclusion

It will be appreciated that certain embodiments (e.g., compositions, kits, method, etc.) may include, incorporate, or otherwise comprise features (e.g., properties, components, ingredients, elements, parts, portions, steps, etc.) described in other embodiments disclosed and/or described herein. Accordingly, the various features of one embodiment can be compatible with, combined with, included in, and/or incorporated into other embodiments of the present disclosure. Disclosure of certain features relative to one embodiment of the present disclosure should not be construed as limiting application or inclusion of said features to the specific embodiment. Rather, it will be appreciated that other embodiments can also include said features without necessarily departing from the scope of the present disclosure.

Moreover, unless a feature is described as requiring another features in combination therewith, any feature described herein may be combined with any other feature of a same or different embodiment disclosed herein.

The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope. Various alterations and/or modifications and additional applications of the features illustrated herein which would occur to one skilled in the relevant art and having possession of this disclosure, can be made to the illustrated embodiments without departing from the spirit and scope of the invention as defined by the claims, and are to be considered within the scope of this disclosure. While various features and embodiments have been disclosed herein, other features and embodiments are contemplated. For instance, well-known features and embodiments are not described herein in particular detail in order to avoid obscuring aspects of the described embodiments. Such features and embodiments are, however, also contemplated herein.

The entirety of International PCT Application Serial No. PCT/US2018/013862, filed Jan. 16, 2018, entitled "Nucleic Acid Preservation Solution and Methods of Manufacture and Use," is incorporated herein by reference.

I claim:

1. A nucleic acid preservation composition, comprising:
   a carrier;
   20-50%, w/w, of a chaotropic agent;
   1-5%, w/w, of a buffering agent;
   0.05-2.5%, w/w, of a chelating agent;
   0.05-2.5%, w/w, of a detergent or a surfactant;
   5-25%, w/w, of an alcohol; and
   0.005-0.25%, w/w, of a mucolytic agent or a reducing agent, the composition having a pH of 7.2-8.8.

2. The composition of claim 1, wherein the composition has a pH of 7.5-8.5.

3. The composition of claim 1, wherein the composition has a pH of 7.8-8.2.

4. The composition of claim 1, wherein the composition is substantially free or devoid of antimicrobial agent(s), bactericidal agent(s), and/or bacteriostatic agent(s) other than the chaotropic agent, the detergent or surfactant, the alcohol, and the mucolytic agent or reducing agent.

5. The composition of claim 1, wherein the composition is substantially free or devoid of inhibitor(s) of ribonuclease other than the chaotropic agent, the detergent or surfactant, the alcohol, and the mucolytic agent or reducing agent.

6. The composition of claim 1, wherein the composition is substantially free or devoid of protease(s).

7. The composition of claim 1, wherein the alcohol comprises a mixture of about 95% ethanol, v/v, and about 5% isopropanol, v/v.

8. The composition of claim 1, wherein:
   the chaotropic agent comprises guanidine thiocyanate;
   the buffering agent comprises tris(hydroxymethyl)aminomethane (Tris);
   the chelating agent comprises ethylenediaminetetraacetic acid (EDTA) or EDTA disodium (salt) dihydrate;
   the detergent or surfactant comprises sodium lauroyl sarcosinate (SLS);
   the alcohol comprises ethanol; and
   the mucolytic agent or reducing agent comprising N-acetyl-L-cysteine (NAC); and the carrier comprising filtered, purified, distilled, and/or deionized water.

9. The composition of claim 1, wherein the composition comprises:
39.53%-48.31%, w/w, of the chaotropic agent;
2.39%-2.92%, w/w, of the buffering agent;
0.73%-0.89%, w/w, of the chelating agent;
0.251%-0.307%, w/w, of the detergent or surfactant;
15.96%-19.50%, w/w, of the alcohol; and
0.084%-0.102%, w/w, of the mucolytic agent or reducing agent.

10. The composition of claim 9, wherein:
the chaotropic agent comprises guanidine thiocyanate;
the buffering agent comprises tris(hydroxymethyl)aminomethane (Tris);
the chelating agent comprises ethylenediaminetetraacetic acid (EDTA) or EDTA disodium (salt) dihydrate;
the detergent or surfactant comprises sodium lauroyl sarcosinate (SLS);
the alcohol comprises ethanol;
the mucolytic agent or a reducing agent comprising N-acetyl-L-cysteine (NAC); and
the carrier comprising filtered, purified, distilled, and/or deionized water.

11. The composition of claim 1, wherein the composition comprises:
43.48%-44.36%, w/w, of the chaotropic agent;
2.62%-2.68%, w/w, of the buffering agent;
0.80%-0.82%, w/w, of the chelating agent;
0.276%-0.282%, w/w, of the detergent or surfactant;
17.55%-17.91%, w/w, of the alcohol; and
0.092%-0.094%, w/w, of the mucolytic agent or reducing agent.

12. The composition of claim 11, wherein:
the chaotropic agent comprises guanidine thiocyanate;
the buffering agent comprises tris(hydroxymethyl)aminomethane (Tris);
the chelating agent comprises ethylenediaminetetraacetic acid (EDTA) or EDTA disodium (salt) dihydrate;
the detergent or surfactant comprises sodium lauroyl sarcosinate (SLS);
the alcohol comprises ethanol;
the mucolytic agent or a reducing agent comprising N-acetyl-L-cysteine (NAC); and
the carrier comprising filtered, purified, distilled, and/or deionized water.

13. A nucleic acid preservation kit, comprising:
a sample collection apparatus comprising a solution compartment; and
the nucleic acid preservation composition of claim 1 disposed in the solution compartment.

14. A nucleic acid preservation kit, comprising:
a sample collection apparatus comprising a solution compartment; and
the nucleic acid preservation composition of claim 2 disposed in the solution compartment.

15. A nucleic acid preservation kit, comprising:
a sample collection apparatus comprising a solution compartment; and
the nucleic acid preservation composition of claim 3 disposed in the solution compartment.

16. A nucleic acid preservation kit, comprising:
a sample collection apparatus comprising a solution compartment; and
the nucleic acid preservation composition of claim 4 disposed in the solution compartment.

17. A nucleic acid preservation kit, comprising:
a sample collection apparatus comprising a solution compartment; and
the nucleic acid preservation composition of claim 5 disposed in the solution compartment.

18. A nucleic acid preservation kit, comprising:
a sample collection apparatus comprising a solution compartment; and
the nucleic acid preservation composition of claim 6 disposed in the solution compartment.

19. A nucleic acid preservation kit, comprising:
a sample collection apparatus comprising a solution compartment; and
the nucleic acid preservation composition of claim 7 disposed in the solution compartment.

20. A nucleic acid preservation kit, comprising:
a sample collection apparatus comprising a solution compartment; and
the nucleic acid preservation composition of claim 8 disposed in the solution compartment.

21. A nucleic acid preservation kit, comprising:
a sample collection apparatus comprising a solution compartment; and
the nucleic acid preservation composition of claim 9 disposed in the solution compartment.

22. A nucleic acid preservation kit, comprising:
a sample collection apparatus comprising a solution compartment; and
the nucleic acid preservation composition of claim 10 disposed in the solution compartment.

23. A nucleic acid preservation kit, comprising:
a sample collection apparatus comprising a solution compartment; and
the nucleic acid preservation composition of claim 11 disposed in the solution compartment.

24. A nucleic acid preservation kit, comprising:
a sample collection apparatus comprising a solution compartment; and
the nucleic acid preservation composition of claim 12 disposed in the solution compartment.

* * * * *